(12) United States Patent
Bridger et al.

(10) Patent No.: US 7,414,065 B2
(45) Date of Patent: *Aug. 19, 2008

(54) METHODS TO MODULATE CONDITIONS MEDIATED BY THE CXCR4 RECEPTOR

(75) Inventors: Gary J. Bridger, Bellingham, WA (US); Eva Maria Boehringer, White Rock (CA); Zhongren Wang, Langley (CA); Dominique Schols, Herent (BE); Renato Tony Skerlj, Newton, MA (US); David Earl Bogucki, Surrey (CA)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/991,944

(22) Filed: Nov. 17, 2004

(65) Prior Publication Data

US 2005/0154005 A1 Jul. 14, 2005

Related U.S. Application Data

(60) Division of application No. 09/743,561, filed as application No. PCT/CA99/00619 on Jul. 8, 1999, now Pat. No. 6,872,714, which is a continuation-in-part of application No. 09/111,895, filed on Jul. 8, 1998, now Pat. No. 6,506,770.

(51) Int. Cl.
*A61K 31/395* (2006.01)
*C07D 257/02* (2006.01)
*A61P 19/02* (2006.01)

(52) U.S. Cl. .................. 514/340; 514/183; 540/474

(58) Field of Classification Search ............. 514/183, 514/340; 540/474
See application file for complete search history.

(56) References Cited

U.S. PATENT DOCUMENTS

| | | | | |
|---|---|---|---|---|
| 5,021,409 | A | 6/1991 | Murrer | 514/183 |
| 5,583,131 | A | 12/1996 | Bridger | 514/183 |
| 5,698,546 | A | 12/1997 | Bridger | 514/183 |
| 5,817,807 | A | 10/1998 | Bridger | 540/474 |
| 6,365,583 | B1 | 4/2002 | MacFarland | 514/183 |
| 2001/0033841 | A1 | 10/2001 | Luster | 424/146.1 |
| 2002/0039993 | A1 | 4/2002 | Winchester | 514/2 |
| 2004/0209837 | A1* | 10/2004 | Kishimoto et al. | 514/44 |
| 2006/0194776 | A1 | 8/2006 | Losordo et al. | |

FOREIGN PATENT DOCUMENTS

| | | |
|---|---|---|
| EP | 0 434 385 | 6/1991 |
| EP | 0 747 368 | 12/1996 |
| EP | 1 072 273 | 1/2001 |
| WO | WO-92/16494 | 10/1992 |
| WO | WO-93/12096 | 6/1993 |
| WO | WO-95/18808 | 7/1995 |
| WO | WO-99/47158 | 9/1999 |
| WO | WO-99/65507 | 12/1999 |
| WO | WO-00/02870 | 1/2000 |
| WO | WO-00/09152 | 2/2000 |
| WO | WO-00/45814 | 8/2000 |

OTHER PUBLICATIONS

Arenburg et al., J. Leukocyte Biol. 62(5):554-562 (1997).
Bertolini et al., Cancer Research (2002) 62:3106-3112.
Bleul et al., "The Lymphocyte Chemoattractant SDF-1 is a Ligand for LESTR/Fusin and Blocks HIV-1 Entry", Nature, 382(6594): 829-832 (1996).
Boshoff et al., "Angiogenic and HIV-Inhibitory Functions of KSHV-Encoded Chemokines", Science, 278(5336):290-294 (1997).
Bradstock et al., Leukemia (2000) 14:882-888.
Bridger et al., "Synthesis and Structure-Activity Relationships of Phenylenebis (methylene)- Linked Bis- Tetraazamacrocycles That Inhibit HIV Replication. Effects of Macrocyclic Ring Size and Substituents on the Aromatic Linker", J. Med. Chem. 38:366-378 (1995).
Bridger et al., "Synthesis and Structure-Activity Relationships of Phenylenebis (methylene)- Linked Bis-Tetraazamacrocycles That Inhibit HIV Replication. 2. Effect of Heteroaromatic Linkers on the Activity of Bicyclams", J. Med. Chem., 39(1):109-119 (1996).
Ponath et al., "Chemokine Receptor Antagonists: Novel Therapeutics for Inflammation and AIDS", Exp. Opin. Invest. Drugs, 7:1-18 (1998).
Rempel et al., Clinical Cancer Research (2000) 6:102-111.
Robledo et al., The Journal of Biological Chemistry (2001) 276(48):45098-45105.
Sanz-Rodriguez et al., Blood (2001) 97(2):346-351.
Schols et al., "Inhibition of T-Tropic HIV Strains by Selective Antagonization of the Chemokine Receptor CXCR4", J. Exp. Med., 186(8):1383-88 (1997).
Schols et al., "Bycyclams, A Class of Potent Anti-HIV Agents, are Targeted at the HIV Coreceptor Fusin/CXCR-4", Antiviral Research, 35:147-156 (1997).
Scotton et al., Cancer Research (2001) 61:4961-4965.
Shen et al., Experimental Hematology (2001) 29:1439-1447.
Tachibana et al., "The Chemokine Receptor CXCR4 is Essential for Vascularization of the Gastrointestinal Tract", Nature, 393:591-94 (1998).
Wyatt et al., "The HIV-1 Envelope Glycoproteins: Fusogens, Antigens, and Immunogens", Science, 280:1884-88 (1998).
Zou et al., "Functions of the Chemokine Receptor CXCR4 in Haematopoiesis and In Cerebellar Development", Nature, 393:595-99 (1998).
Burger et al., Blood (2000) 96(8):2655-2663.
Burger et al., Blood (1999) 94(11):3658-3667.

(Continued)

*Primary Examiner*—Brenda L Coleman
(74) *Attorney, Agent, or Firm*—Morrison & Foerster LLP

(57) ABSTRACT

The present invention is drawn to novel antiviral compounds, pharmaceutical compositions and their use. More specifically this invention is drawn to derivatives of monocyclic polyamines which have activity in standard tests against HIV- or FIV-infected cells as well as other biological activity related to binding of ligands to chemokine receptors that mediate a number of mammalian embryonic developmental processes.

8 Claims, 9 Drawing Sheets

OTHER PUBLICATIONS

Carroll et al. "Differential Regulation of HIV-1 Fusion Cofactor Expression by CD28 Costimulation of CD4+ T Cells", Science, 276(5310):273-276 (1997).
Chemical Abstracts, 113:40649 (1990).
Chemical Abstracts, 111:190197 (1987).
Chemical Abstracts, 123:56538 (1994).
De Bont et al., Cancer Research (2001) 61:7654-7659.
De Clerco et al., "Highly Potent and Selective Inhibition of Human Immunodeficiency Virus by the Byclam Derivative JM3100", Antimicrobial Agents & Chemotherapy, 38(4):668-674 (1994).
Devries et al., Seminars in Immunology (1999) 11:95-104.
Donzella et al., "AMD3100, A Small Molecule Inhibitor of HIV-1 Entry Via the CXCR4 Co-Receptor", Nature Medicine, 4(1):72-77 (1998).
Durig et al., Leukemia (2001) 15:752-756.
Fukuyama et al., "2- and 4-Nitrobenzenesulfonamides: Exceptionally Versatile Means for Preparation of Secondary Amines and Protection of Amines", Tetrahedron Letters, 36(36):6373-74 (1995).
Gazitt and Liu, Stem Cells (2001) 19:37-45.
Geminder et al., The Journal of Immunology (2001) 167:4747-4757.
Gupta et al., "Chemokine Receptors In Human Endothelial Cells", J. Biological Chem., 273(7):4282-87 (1998).
Hesselgesser et al., J. of Biol. Chem. (1998) 273(25):15687-15692.
Hoxie et al., "CD4-Independent Infection by HIV-2 is Mediated by Fusin/CXCR4", Cell, 87:745-756 (1996).
International Search Report for PCT/CA99/00619, Oct. 1999.
Joao et al. "Quantitative Structural Activity Relationship Study of Bis-Tetraazacyclic Compounds. A Novel Series of HIV-1 and HIV-2 Inhibitors", J. Med. Chem. 38:3865-73 (1995).
Koshiba et al., Clinical Cancer Research (2000) 6:3530-3535.
Lagneaux et al., Poster session: Bone Marrow Stroma and Marrow Failure, Saturday, Jul. 6, 2002, Abstract #72.
Leff, "Besides Aiding AIDS Entry, Receptor Honchos Fetal Growth of Brain, Gut, Blood Systems", Bioworld Today, 9:111 (1998).
Libura et al., Blood (2002) 100(7):2597-2606.
Martin et al., Helv Chem. Chem. Soc. 73:149-153 (1990).
Miedema et al., "Changing Virus-Host Interactions in the Course of HIV-1 Infection", Immunological Reviews, 140:35-72 (1994).
Mohle et al., Blood (1998) 91(12):4523-4530.
Moore et al., Journal of Investigative Medicine (1998) 46(4):113-120.
Morphy et al., "Towards Tumour Targeting with Copper-Radiolabelled Macrocycle-Antibody Conjugates: Synthesis, Antibody Linkage, and Complexation Behaviour", J. Chem. Soc. Perkin Trans., 2:573-85 (1990).
Muller et al., Nature (2001) 410:50-56.
Oberlin et al. "The CXC Chemokine SDF-1 is the Ligand for Lestr/Fusin and Prevents.
Hesselgesser et al., Journal of Biological Chemistry (1998) 273(25):15687-15692.
Horuk et al., Chemokine Receptors, Cytokine and Growth Factor Reviews (2001) 12(4):313-355.

* cited by examiner

AMD3465

AMD3538

AMD3500

AMD3499

AMD3498

AMD3497

AMD3516

AMD3530

AMD3517

AMD3544

AMD3543

AMD3529

AMD7049

AMD7050

AMD7051

AMD7059

AMD7063

AMD7060

AMD7058

AMD7061

AMD7032

AMD3451

AMD7048

AMD3454

AMD3472

AMD3526

AMD3100

AMD3484

AMD8630

AMD7097

AMD8631

AMD-Exp 1

AMD7450

AMD-Exp 2

AMD7463

AMD-Exp 3

METHODS TO MODULATE CONDITIONS MEDIATED BY THE CXCR4 RECEPTOR

CROSS-REFERENCE TO RELATED APPLICATION

This application is a divisional of U.S. Ser. No. 09/743,561 filed 13 Aug. 2001, now U.S. Pat. No. 6,872,714, which is a U.S. National Stage of PCT/CA99/00619, filed 8 Jul. 1999, which is a continuation-in-part of U.S. application Ser. No. 09/111,895, filed 8 Jul. 1998, now U.S. Pat. No. 6,506,770.

The present invention is drawn to novel antiviral compounds, pharmaceutical compositions and their use. More specifically this invention is drawn to derivatives of monocyclic polyamines which have activity in standard tests against HIV-infected cells as well as other biological activity related to binding of ligands to chemokine receptors that mediate a number of mammalian embryonic developmental processes. The present invention further includes methods of treating various diseases mediated by chemokine receptor-ligand binding.

BACKGROUND OF THE INVENTION

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs*, 7:1-18, 1998). These chemotactic cytokines, or chemokines, constitute a family of proteins, approximately 8-10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR"; while those of the α-chemokines are designated "CXCR".

Chemokines are considered to be principal mediators in the initiation and maintenance of inflammation. More specifically, chemokines have been found to play an important role in the regulation of endothelial cell function, including proliferation, migration and differentiation during angiogenesis and re-endothelialization after injury (Gupta et al., *J. Biolog. Chem.*, 7:4282-4287, 1998). Two specific chemokines have been implicated in the etiology of infection by human immunodeficiency virus (HIV).

In most instances, HIV initially binds via its gp120 envelope protein to the CD4 receptor of the target cell. A conformational change appears to take place in the gp120 which results in its subsequent binding to a chemokine receptor, such as CCR-5 (Wyatt et al., *Science*, 280:1884-1888 (1998)). HIV-1 isolates arising subsequently in the infection bind to the CXCR-4 chemokine receptor. In view of the fact that the feline immunodeficiency virus, another related retrovirus, binds to a chemokine receptor without needing to bind first to the CD4 receptor, suggests that chemokine receptors may be the primordial obligate receptors for immunodeficiency retroviruses (Richardson et al., *J. Virol.* 73:661 (1999)).

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll et al., *Science*, 276: 273-276 1997). During the course of infection within a patient, it appears that a majority of HIV particles shift from the M-tropic to the more aggressive T-tropic viral phenotype (Miedema et al., *Immune. Rev.*, 140:35 (1994)). Curiously, the M-tropic viral phenotype correlates with the virus's ability to enter the cell following binding of the CCR-5 receptor, while the T-tropic viral phenotype correlates with viral entry into the cell following binding and membrane fusion with the CXCR-4 receptor. Clinically observations suggest that patients who possess genetic mutations in the CCR-5 appear resistant or less susceptible to HIV infection.

However, the binding of chemokine receptors to their natural ligands appears to serve a more evolutionary and central role than only as mediators of HIV infection. The chemokine receptor, CXCR-4 has been found to be essential for the vascularization of the gastrointestinal tract (Tachibana et al., *Nature*, 393:591-594 (1998)) as well as haematopoiesis and cerebellar development (Zou et al., *Nature*, 393:595-599 (1998)). Interference with any of these important functions served by the binding of pre-B-cell growth-stimulating factor/stromal derived factor (PBSF/SDF-1) to the CXCR-4 chemokine receptor results in lethal deficiencies in vascular development, haematopoiesis and cardiogenesis. Similarly, fetal cerebellar development appears to rely upon the effective functioning of CXCR-4 in neuronal cell migration and patterning in the central nervous system. This G-protein-coupled chemokine receptor appears to play a critical role in ensuring the necessary patterns of migration of granule cells in the cerebellar anlage. Interactions of SDF-1 and CXCR4 are also important in maintaining B-cell lineage and in retaining stem cells in bone marrow (Peled et al., *Science* 283: 845 (1999); Springer et al., *Immunity* 10:463 (1999)).

In attempting to better understand the relationship between chemokines and their receptors, recent experiments to block the binding of HIV to the CXCR-4 chemokine receptor were carried out through the use of monoclonal antibodies or small molecules that appear to suggest a useful therapeutic strategy (Schols et al., *J. Exp. Med.* 186:1383-1388 (1997); Schols et al., *Antiviral Research* 35:147-156 (1997)). Small molecules, such as bicyclams, appear to specifically interfere with the CXCR-4 binding and not CCR-5 binding (Donzella et al., *Nature Medicine*, 4:72-77 (1998)). These experiments demonstrated interference with HIV entry and membrane fusion into the target cell in vitro. Additional experiments monitoring the calcium flux or $Ca^{2+}$ mobilization assay demonstrated that a bicyclam also functioned as an antagonist to signal transduction resulting from the binding of stromal derived factor or SDF-1α, the natural chemokine to CXCR-4.

Further, the etiology or association of chemokine receptor binding in the proliferation of glioblastoma tumor cells has been reported by Sehgal et al., *J. of Surg. Oncolo.* 69:99-104 (1998) ("Sehgal I") and Sehgal et al., *J. of Surg. Oncolo.* 69: 239-248 (1998) ("Sehgal II"). The role of CXCR4 of its binding to its receptor appears to play a significant role in the formation and/or proliferation of glioblastoma cells. The inhibition of the binding by CXCR4 to its natural receptor ligand by compounds of the present invention, such as AMD 3100, offer a new drug in the treatment tumors of central nervous system that are mediated or associated with chemokines, such as CXCR4.

Additionally, CXC chemokines have been found to regulate or are associated with the regulation of angiogenesis in non-small cell lung cancer (see: Arenberg, et al., *J. of Leukocyte Biol.*; 62:554562 (1997); and Moore et al. *TCM*, vol 8(2): 51-58 (1998) Elsevier Science, Inc.). The role of CXC chemokines and the binding to their respective receptors appear to play a significant role in the formation and/or proliferation of non-small cell lung cancer. The inhibition of the binding of these CXC chemokines to their natural receptor ligands by compounds of the present invention, such as AMD 3100, offer a new drug in the treatment tumors such as non-small cell lung cancer that are mediated or associated with increased levels of chemokines.

U.S. Pat. Nos. 5,583,131, 5,698,546 and 5,817,807 disclose cyclic compounds that are active against HIV-1 and HIV-2 in in vitro tests. We have now discovered that these compounds exhibit anti-HIV (anti-human immunodeficiency virus) and anti-FIV (anti-feline immunodeficiency virus) activities due to their binding to the chemokine receptor 4 (CXCR-4 or Fusin receptor), expressed on the surface of certain cells of the immune system (Este et al., *Mol. Pharmacol.* 55:67 (1999); Egberink et al, *J. Virol in press* (1999)). This competitive binding thereby protects these target cells from infection by HIV which utilize the CXCR-4 receptor for entry. We have discovered that the disclosed compounds also antagonize the binding, signaling and chemotactic effects of the natural CXC-chemokine for CXCR-4, stromal cell-derived factor 1α (SDF-1α). Herein, we further disclose novel compounds that demonstrate protective effects against HIV infection of target cells by inhibition of binding in vitro to the CC-5 receptor (CCR-5).

SUMMARY OF THE INVENTION

The present invention provides novel compounds, that demonstrate protective effects on target cells from HIV infection as well as demonstrate other biological activities related to the ability of these compounds to inhibit the binding by the natural ligand to its chemokine receptor.

Accordingly, the present invention provides a macrocyclic compound of formula I:

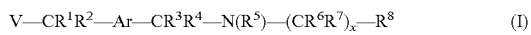   (I)

wherein V is a cyclic polyamine moiety having a total of 9 to 24 members and from 2 to 6, but preferably from 3 to 6, optionally substituted amino nitrogens optionally substituted amine nitrogens spaced by two or more optionally substituted carbon atoms from each other, and which may optionally comprise a fused aromatic or heteroaromatic ring;

$R^1$ to $R^7$ may be the same or different and are independently selected from hydrogen or straight, branched or cyclic $C_{1-6}$alkyl;

$R^8$ is a heterocyclic group, a substituted aromatic group, or a mercaptan group;

Ar is an aromatic or heteroaromatic ring each optionally substituted at single or multiple positions with electrons-donating or withdrawing groups;

x is 1 or 2;

and the acid addition salts and metal complexes thereof.

Preferably V is a 14- to 17 membered fused or unfused ring system, such as a cyclam system or a 4,7,10,17-tetraazabicyclo[13.3.1]heptadeca-1(17),13,15-triene system or a derivative thereof, and especially a cyclam system or derivative thereof. The moiety V may be substituted at C or N non-linking atoms, suitably by hydroxyl, alkoxy, thiol, thioalkyl or any other atom or group which does not adversely affect the activity or toxicity of the compounds but may reduce the basicity of the amines, for example halogen, nitro, carboxy, carboxyamido, sulphonic acid or phosphate. Suitably the fused aromatic or heteroaromatic ring is phenyl, pyridine, pyrimidine, pyrazine, imidazole or thiazole. Preferably, the fused aromatic or heteroaromatic ring is phenyl or pyridine.

Preferably $R^1$ to $R^7$ are each hydrogen.

Preferably $R^8$ is selected from pyridine, pyrimidine, pyrazine, imidazole, thiophene, thiophenyl, aminobenzyl, piperidinyl, piperazinyl or a mercaptan group.

Preferably Ar is phenyl. Preferred substituents are alkyl, aryl, amino, alkoxy, hydroxy, halogen, carboxyl and carboxamido.

The invention also includes what may be termed as "prodrug", that is protected forms of the compounds, which release the compound after administration to a patient. For example, the compound may carry a protective groups which is split off by hydrolysis in body fluids e.g. in the bloodstream, thus releasing active compound or are oxidized or reduced in body fluids to release the compound. A discussion on pro-drugs may be found in "Smith and Williams' Introduction to the Principles of Drug Design", H. J. Smith, Wright, Second Edition, London 1988.

Acid addition salts, for example hydrochlorides, and non-toxic labile metal complexes of compounds of formula I are also active compounds according to the present invention. Non-toxic in the present tense has to be considered with reference to the prognosis for the infected patient without treatment. Copper and zinc complexes are preferred although other metals such as nickel may be considered, whereas less labile metals such as cobalt and rhodium are less preferred because of likely lower selectivity.

Compounds of formula I are novel. Accordingly, a further aspect of the invention provides a process for the preparation of a compound of formula I which comprises the following steps:

(i) nucleophilic attack by the cyclic polyamine V having a single unprotected amine nitrogen, all other amine nitrogen atoms being protected, on an excess of a compound of formula II

   (II)

wherein $R^1$ to $R^4$ and Ar are as hereinbefore defined, and each Y is an active substituent which can be displaced by the unprotected nitrogen of polyamine V and is preferably selected from Br, Cl, I, methane sulphonate, 4-toluenesulphonate, trifluoromethane sulphonate.

It is well within the capabilities and knowledge of the skilled synthetic chemist to protect the amine nitrogens of cyclic polyamines, and it is preferred to use substitution by methanesulphonyl and/or toluenesulphonyl and/or diethoxyphosphoryl (see: Bridger et al, *J. Med. Chem.*, 38:366-378 (1995); Bridger et al, U.S. Pat. No. 5,583,131 or Bridger et al, U.S. Pat. No. 5,698,546) and/or nitrobenzenesulfonyl (Fukuyama et al., *Tetrahedron Letters* 1995, 36, 6373-6374.

The protected polyamine V is firstly reacted with a 5-to 10-fold excess of a compound of formula II in a solvent such as acetonitrile or dimethylformamide, tetrahydrofuran or dioxane and in the presence of a base, for example sodium carbonate or potassium carbonate. The reaction generally proceeds at room temperature to elevated temperature to give a cyclic polyamine in which all amine nitrogens are protected. In general, a mixture of products will be obtained and we have found that the product can conveniently be purified by silica gel chromatography or crystallization.

Nucleophilic attack of a compound of formula III

   (III)

wherein $R^5$ to $R^8$ and x are as hereinbefore defined on the product of the reaction described at (I) above, and subsequently de-protecting the amine nitrogens. The reaction with an excess of a compound of formula III is carried out under similar conditions to the reaction with the polyamine V.

The de-protection step is suitably carried out by re-fluxing the protected molecule in a mixture of aqueous HBr and acetic acid or concentrated sulphuric acid, or in the case of diethoxyphosphoryl in the presence of gaseous hydrogen chloride or gaseous hydrogen bromide in acetic acid; in the case of nitrobenzenesulfonyl deprotection, a mercaptan such as thiophenol or mercaptoacetic acid in the presence of a suitable base such as potassium carbonate, cesium carbonate, sodium hydroxide or lithium hydroxide in a solvent such as dimethylformamide, acetonitrile, tetrahydrofuran or dioxane is used. This reaction generally proceeds at room temperature to elevated temperatures to give a polyamine in which the nitrogens are deprotected. Alternatively, and accordingly, a further aspect of the invention provides a process for the preparation of compounds of Formula I which comprises the following steps:

(i) nucleophilic attack by the cyclic polyamine V having a single unprotected amine nitrogen, all other amine nitrogens being protected, with an excess of a compound of formula (IV)

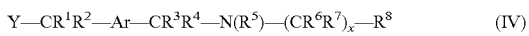

Wherein $R^1$ to $R^4$ and x, $R^6$ to $R^8$ and Ar are as hereinbefore defined and Y is an active substituent which can be displaced by the unprotected nitrogen of cyclic polyamine V as hereinbefore defined. In this case, the intended substituent $R^5$ is hydrogen but for convenience, the nitrogen is protected as a nitrobenzenesulfonyl or diethoxyphosphoryl group.

The protected polyamine V is first reacted with a compound of formula IV using similar conditions to the reactions with compounds of formula II and formula III as described above and the product of this reaction is subjected to deprotection of the amine nitrogens on the polyamine and at $R^5$.

The deprotection steps were carried out as described above. For convenience, a sequential combination of these deprotection reactions may be used when a mixture of any of: methanesulphonyl; toluenesulphonyl; diethoxyphosphoryl; or nitrobenzenesulfonyl groups are present.

The novel compounds further comprise a macrocyclic compound of general formula V:

where $V^2$ is a cyclic polyamine moiety having a total of 9 to 24 members and from 2 to 6, but preferably from 3 to 6, optionally substituted amine nitrogens spaced by two or more optionally substituted carbon atoms from each other, and which may optionally comprise a fused aromatic or heteroaromatic ring; where $R^9$ and $R^{10}$ may be the same or different and are independently selected from hydrogen or straight, branched or cyclic $C_{1-6}$ alkyl; further, where $Ar^2$ is an aromatic, fused aromatic, heterocyclic or fused heterocyclic ring each optionally substituted at single or multiple positions with electron-donating or withdrawing groups and/or aromatic and heterocyclic groups and their alkyl derivatives thereof; and the acid addition salts and metal complexes.

These novel compounds have demonstrated anti-HIV activity in an in vitro screen assay as presented in Table 1. These novel compounds have also demonstrated biological activity in inhibiting CXCR-4 specific monoclonal antibody (12G5) from binding to CXCR-4 on SUP-T1 cells by AMD compounds. These data are shown in Table 2 for AMD3100 (1,1'-[1,4-phenylenebis(methylene)]bis-1,4,8,11-tetraazacyclotetradecane), AMD3465 (N-[1,4,8,11-tetraazacyclotetradecanyl-1,4-phenylenebis(methylene)]-2-(aminomethyl)pyridine) and six new compounds: AMD 7049; AMD 7050; AMD 7051; AMD 7058; AMD 7059; and AMD 7063.

Data showing inhibition of the increased Ca2+ flux induced by SDF-1 in SUP-T1 cells (inhibition of signal transduction) by AMD compounds are shown in Table 3 for AMD3100, AMD3465 and compounds: AMD 7049; AMD 7050; AMD 7051; AMD 7058; AMD 7059; and AMD 7063.

Several novel compounds also inhibited infection of the cell line U87.CD4.CCR5 by the M-tropic HIV-1 strain BaL, which exclusively utilizes the CCR-5 co-receptor for entry. These data are shown in Table 4.

The experimental procedures for the mAb binding assay, the inhibition of $Ca^{2+}$ flux, and inhibition of infection by the HIV-1 BaL strain in U87.CD4.CCR5 cells would be readily understood by the skilled artisan. For example, see: Schols et al., *J. Exp. Med* 186:1383-1388 (1997); Schols et al., *Antiviral Research* 35:147-156 (1997); and Donzella et al., *Nature Medicine*, 4:72-77 (1998). Also, the characterization of the CXCR-4 specific monoclonal antibody 12G5 is taught by Hoxie et al., *Cell*, 87:745-756 (1996).

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

Having now generally described the invention, the same will be more readily understood through reference to the following examples which are provided by way of illustration, and are not intended to be limiting of the present invention, unless specified.

As mentioned above, the compounds of the invention have activity against viral infections, especially retrovirus infections and specifically HIV. Accordingly, a further aspect of the invention provides a compound of formula I or formula V for use in medicine. More specifically, there is provided the use of a compound of formula I or formula V in the manufacture of a medicament for the treatment of HIV-infected patients. In the alternative, there is provided a method of treating an HIV-infected patient comprising administering to said patient, a pharmaceutically effective amount of a compound of formula I or formula V. Although compounds of formula I or formula V could be administered as the raw material, it is preferable to present them in the form of a pharmaceutical composition comprising a compound of formula I or formula V as active ingredient in admixture with a pharmaceutically acceptable diluent or carrier and optionally one or more other therapeutic ingredients, such compositions providing a further aspect of the invention.

In all aspects of the invention, it is understood that meso forms, enantiomers and resolved optically active forms of the compounds of formula I or formula V are also included. Also, it is to be considered within the invention, compounds of formula I or formula V diluted with non-toxic or other active substances.

DETAILED DESCRIPTION OF THE INVENTION

Figure 1:
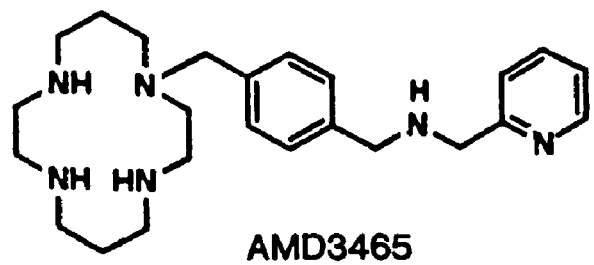
FIG. 1, shows the structural formula of compound AMD 3465.
Figure 2:
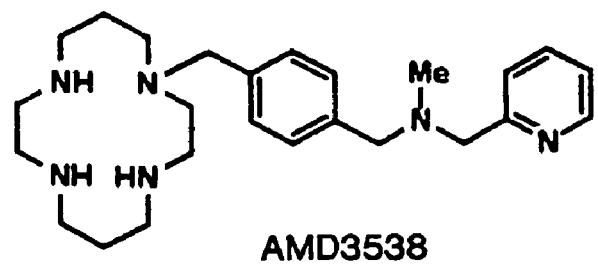
FIG. 2, shows the structural formula of compound AMD 3538.
Figure 3:
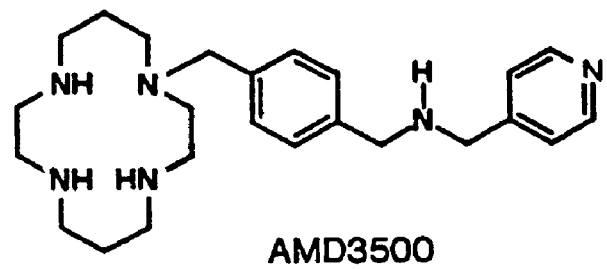
FIG. 3; shows the structural formula of compound AMD 3500.
Figure 4:
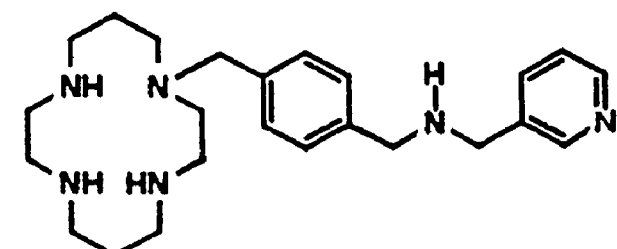
FIG. 4, shows the structural formula of compound AMD 3499.
Figure 5:
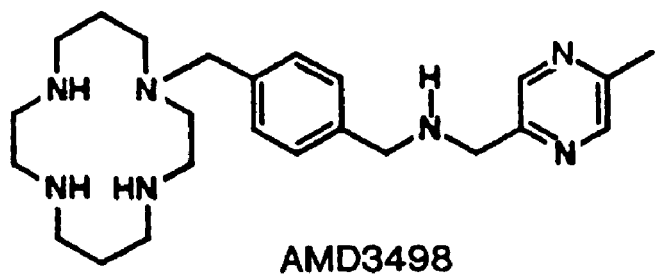
FIG. 5; shows the structural formula of compound AMD 3498.
Figure 6:
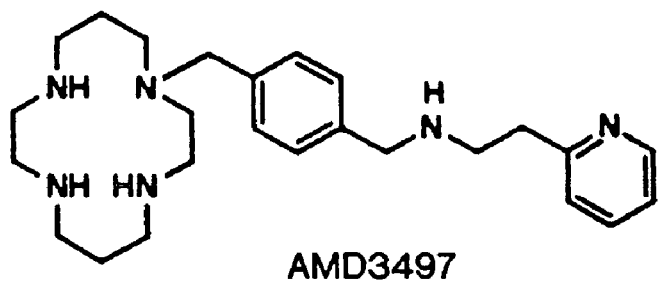
FIG. 6; shows the structural formula of compound AMD 3497.
Figure 7:
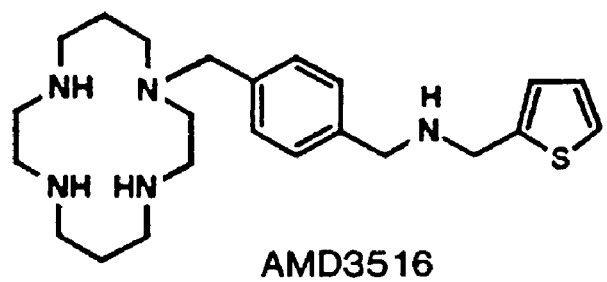
FIG. 7; shows the structural formula of compound AMD 3516.
Figure 8:
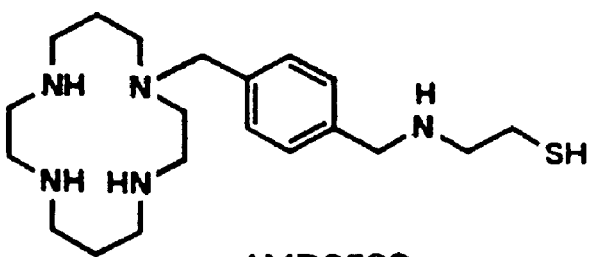
FIG. 8; shows the structural formula of compound AMD 3530.
Figure 9:
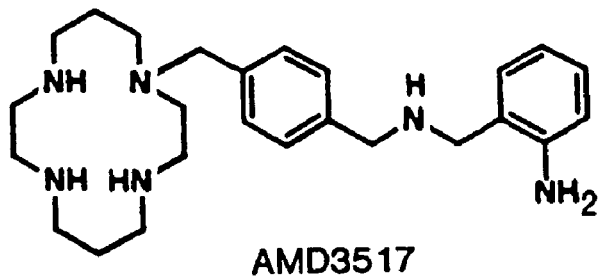
FIG. 9; shows the structural formula of compound AMD 3517.
Figure 10:
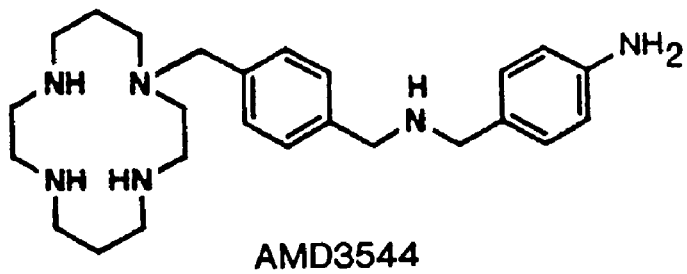
FIG. 10; shows the structural formula of compound AMD 3544.
Figure 11:
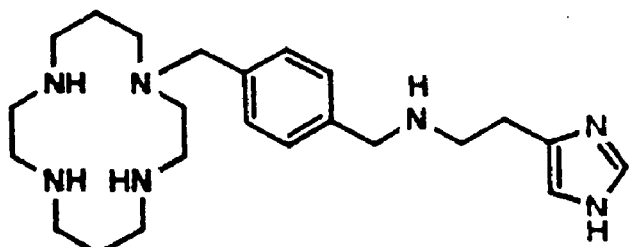
FIG. 11; shows the structural formula of compound AMD 3543.
Figure 12:
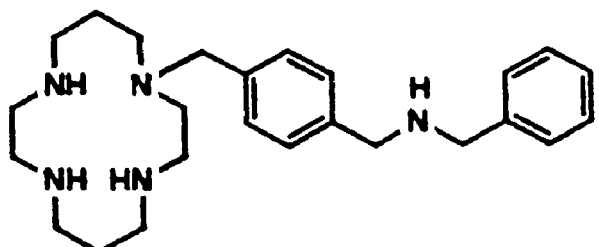
FIG. 12; shows the structural formula of compound AMD 3529.
Figure 13:
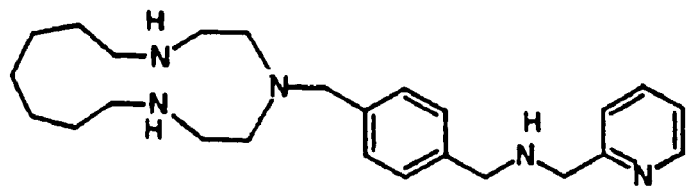
FIG. 13; shows the structural formula of compound AMD 7049.
Figure 14:
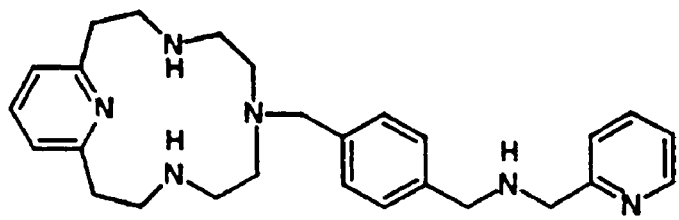
FIG. 14; shows the structural formula of compound AMD 7050.
Figure 15:
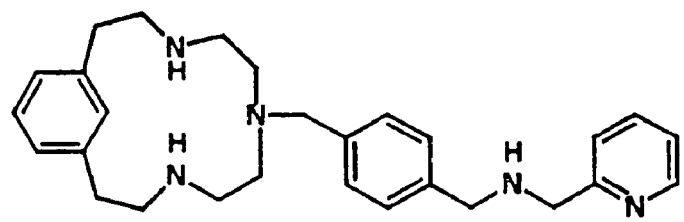
FIG. 15; shows the structural formula of compound AMD 7051.
Figure 16:
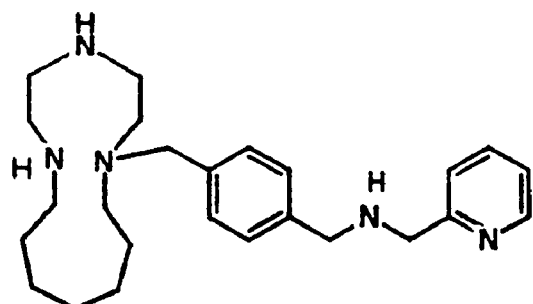
FIG. 16; shows the structural formula of compound AMD 7059.
Figure 17:
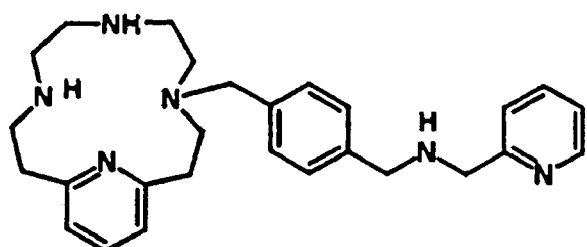
FIG. 17; shows the structural formula of compound AMD 7063.
Figure 21:
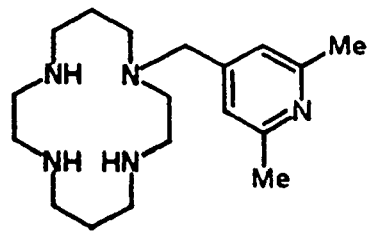
FIG. 21; shows the structural formula of compound AMD 7060.
Figure 18:
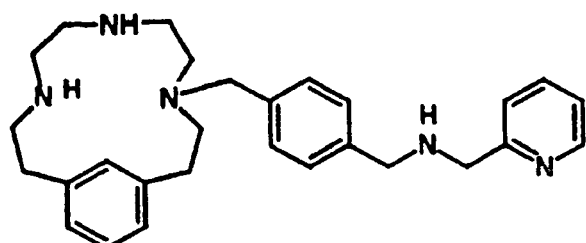
FIG. 18; shows the structural formula of compound AMD 7058.
Figure 22:
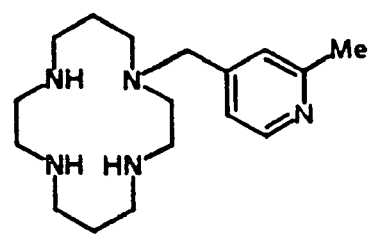
FIG. 22; shows the structural formula of compound AMD 7061.
Figure 19:
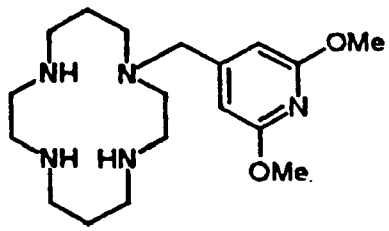
FIG. 19; shows the structural formula of compound AMD 7032.
Figure 23:
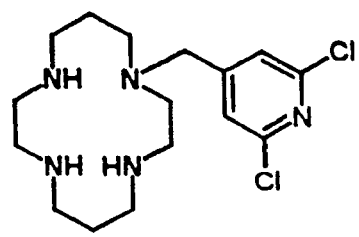
FIG. 23; shows the structural formula of compound AMD 3451.
Figure 20:
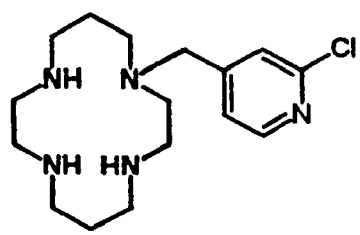
FIG. 20; shows the structural formula of compound AMD 7048.
Figure 24:
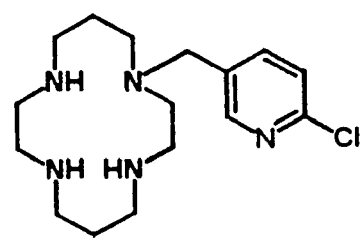
FIG. 24; shows the structural formula of compound AMD 3454.
Figure 25:
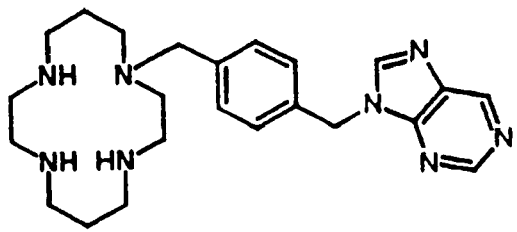
FIG. 25; shows the structural formula of compound AMD 3472.
Figure 26:
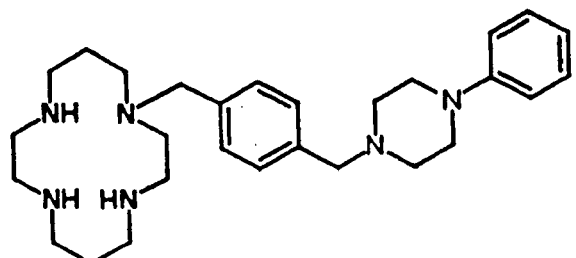
FIG. 26; shows the structural formula of compound AMD 3526.

Terms as used herein are based upon their art recognized meaning unless otherwise indicated and should be clearly understood by the ordinary skilled artisan. The present invention will now be illustrated by the following preparative Examples.

General Procedure A

1-[1-Methylene-4-(bromomethylene)phenylene]-4,8,11-tris(diethoxyphosphoryl)-1,4,8,11-tetraazacyclotetradecane To a stirred solution of 4,8,11-Tris(diethoxyphosphoryl)-1,4,8,11-tetraazacyclotetradecane (See Bridger et al. *J Med. Chem.* 1995, 38, 366-378) (6.1 g, 0.01 mol) and $K_2CO_3$ (1.89 g, 0.013 mol) in $CH_3CN$ (150 ml) was added α,α'-dibromo-p-xylene (13.2 g, 0.05 mol) and the reaction mixture stirred at 70° C. for 1 hour. The solution was cooled to room temperature and the solvent removed under reduced pressure. The residue was partitioned between brine (50 ml) and $CH_2Cl_2$ (100 ml). The organic phase was separated, dried ($Na_2SO_4$) and concentrated to a minimum volume. The solid was filtered off and the solvent evaporated under reduced pressure to give the crude product as a pale yellow oil. Purification by column chromatography in silica gel ($CH_2Cl_2\backslash CH_3OH$, 25:1) gave 1-[1-methylene-4-(bromomethylene)phenylene]-4,8,11-tris(diethoxyphosphoryl-1,4,8,11-tetraazacyclotetra-decane (4.7 g, 59%) as a pale yellow oil. $^1H$ NMR ($CDCl_3$) δ 1.21-1.37 (m, 18H), 1.66-1.74 (m, 2H), 1.82-1.91 (m, 2H), 2.30-2.35 (m, 2H), 2.58-2.63 (m, 2H), 2.99-3.16 (m, 12H), 3.48 (s, 2H), 3.95-4.07 (m, 12H), 4.48 (s, 2H), 7.21-7.35 (4H).

General Procedure B

Second Alkylation of the Bromobenzyl Cyclam Intermediate with an Amine (see for Example: Bridger et al. *J. Med. Chem.* 1995, 38, 366-378)

To a solution of the appropriate amine (5.0 equiv.) in dry $CH_3CN$ (5 mL) containing a suspension of $K_2CO_3$ (1.5 equiv.) at 80° C. was added dropwise with stirring a solution of 1-[1-methylene-4-(bromomethylene)phenylene]-4,8,11-tris(diethoxyphosphoryl-1,4,8,11-tetraazacyclotetradecane (0.6 mmol) in $CH_3CN$ (10 ml) over 15-20 min. After stirring for a further 1 hour at 80° C. the solution was concentrated to dryness and the residue was partitioned between $CH_2Cl_2$ and water. The organic layer was separated and washed with water (3×) then dried ($MgSO_4$) and evaporated. The crude residue was purified by column chromatography on silica gel eluting with 5-15% $MeOH/CH_2Cl_2$ to afford a viscous oil.

General Procedure C

De-protection of the Diethoxyphosphoramidate Groups Using HBr/HOAc at Room Temperature (see for Example: Bridger et al. *J. Med. Chem.* 1995, 38, 366-378)

To a stirred solution of the protected cyclam derivative from procedure B (0.1-0.5 mmol) in acetic acid (3 mL) was added 30% HBr in acetic acid (Aldrich, 5 mL) and the solution was stirred at room temperature for 14 hours. The resulting precipitate was collected by filtration and washed with acetic acid then $Et_2O$. The solid was then dissolved in $H_2O$ (3 mL) and treated with charcoal (100 mg) and the mixture was heated to 80° C. for 30 min. The hot solution was filtered through celite and the filtrate was concentrated to approximately 1 mL after which acetic acid was added resulting in the immediate formation of a white precipitate. The white solid was collected by filtration and dried in vacuo.

The following compounds were prepared by these methods:

EXAMPLE 1

N-[1,4,8,11-Tetraazacyclotetradecanyl-1,4-phenylenebis(methylene)]-2-(amino-methyl)pyridine hexahydrobromide (AMD 3465)

White solid: Mp 200-205° C. (dec); $^1$H NMR (D$_2$O) δ 2.04 (m, 4H), 3.20-3.40 (m, 8H), 3.40-3.60 (m, 8H), 4.34 (s, 2H), 4.38 (s, 2H), 4.51 (s, 2H), 7.50 (m, 4H), 7.75 (t, 1H, J=6.6 Hz), 7.82 (d, 1H, J=7.9 Hz), 8.26 (t, 1H, J=7.9 Hz), 8.63 (d, 1H, J=5.3 Hz); $^{13}$C NMR (D$_2$O) δ 18.30, 18.96, 37.04, 37.28, 37.40, 40.92, 41.13, 41.49, 44.26, 47.61, 48.01, 51.29, 58.88, 127.46, 127.75, 130.40, 131.05, 131.23, 131.47, 132.10, 132.44, 144.95, 145.81, 146.01; FAB MS m/z 493 (M+H$^{81}$Br, 7), 491 (M+H$^{79}$Br, 7), 411 (M+H, 100).

Anal. (C$_{24}$H$_{38}$N$_6$.6HBr); Calc. C, 32.36; H, 4.98; N, 9.44; Br, 53.21. Found C, 32.20; H, 5.00; N, 9.30; Br, 53.10.

EXAMPLE 2

N-[1,4,8,11-Tetraazacyclotetradecanyl-1,4-phenylenebis(methylene)]-N-methyl-2-(aminomethyl)pyridine hexahydrobromide hydrate (AMD 3538)

White solid: Mp 220-225° C. (dec); $^1$H NMR (D$_2$O) δ 2.06 (m, 4H), 2.76 (s, 3H), 3.20-3.65 (m, 16H), 4.47 (bs, 4H), 4.65 (s, 2H), 7.54 (bs, 4H), 7.80 (t, 1H), 7.87 (d, 1H), 8.28 (t, 1H), 8.68 (d, 1H); $^{13}$C NMR (D$_2$O) δ 18.14, 18.75, 18.89, 36.74, 37.04, 37.15, 37.62, 40.38, 40.72, 40.91, 41.28, 44.05, 47.50, 56.98, 58.88, 60.28, 127.60, 128.86, 130.78, 130.96, 132.16, 132.64, 144.91, 145.04, 146.12; FAB MS m/z 507 (M+H$^{81}$Br, 27), 507 (M+H$^{79}$Br, 22), 425 (M+H, 100). Anal. (C$_{25}$H$_{40}$N$_6$.6HBr.1.5H$_2$O); Calc. C, 32.04; H, 5.27; N, 8.97; Br, 51.16. Found C, 31.88; H, 5.30; N, 8.93; Br, 51.00.

EXAMPLE 3

N-[1,4,8,11-Tetraazacyclotetradecanyl-1,4-phenylenebis(methylene)]-4-)amino-methyl)pyridine hexahydrobromide (AMD 3500)

White solid: mp 201-204° C. (dec); $^1$H NMR (D$_2$O) δ 1.91-2.12 (m, 4H), 3.00-3.49 (m, 16H), 4.13 (s, 2H), 4.34 (s, 2H), 4.53 (s, 2H), 7.39-7.57 (m, 4H), 8.02 (d, 2H, J=6.3 Hz), 8.74 (d, 2H, J=6.3 Hz); $^{13}$C NMR (D$_2$O) δ 18.26, 18.88, 36.94, 37.29, 37.36, 40.89, 41.06, 41.44, 44.21, 47.61, 49.17, 51.43, 59.02, 127.84, 130.21, 131.64, 132.15, 132.45, 142.19, 151.67; FAB MS m/z 493 (M+H$^{81}$Br, 8), 491 (M+H$^{79}$Br, 10), 411 (M+H, 83), 320 (37), 247 (58), 201 (100). Anal. (C$_{24}$H$_{38}$N$_6$.6HBr); Calc. C, 32.17; H, 4.95; N, 9.34; Br, 53.50. Found C, 32.16; H, 5.03; N, 9.41; Br, 53.28.

EXAMPLE 4

N-[1,4,8,11-Tetraazacyclotetradecanyl-1,4-phenylenebis(methylene)]-3-(amino-methyl)pyridine hexahydrobromide (AMD 3499)

White solid: mp 198-202° C. (dec); $^1$H NMR (D$_2$O) δ 1.83-2.07 (m, 4H), 2.96-3.47 (m, 16H), 4.11 (s, 2H), 4.32 (s, 2H), 4.49 (s, 2H), 7.38-7.56 (m, 4H), 8.04 (t, 1H, J=6.4 Hz), 8.63 (d, 1H, J=8.3 Hz), 8.76 (d, 1H, J=5.6 Hz), 8.86 (s, 1H); $^{13}$C NMR (D$_2$O) δ 18.23, 18.87, 36.92, 37.29 (2C), 40.88, 41.05, 41.43, 44.17, 47.22, 47.60, 51.18, 59.04, 128.29, 130.01, 131.49, 132.14, 132.66 (2C), 142.55, 142.76, 148.98; FAB MS m/z 493 (M+H$^{81}$Br, 7), 491 (M+H$^{79}$Br, 6), 411 (M+H, 100), 320 (33), 247 (24). Anal. (C$_{24}$H$_{38}$N$_6$.6HBr); Calc. C, 32.17; H, 4.95; N, 9.34; Br, 53.50. Found C, 32.08; H, 5.02; N, 9.25; Br, 53.28.

EXAMPLE 5

N-[1,4,8,11-Tetraazacyclotetradecanyl-1,4-phenylenebis(methylene)]-(2-amino-methyl-5-methyl)pyrazine pentahydrobromide (AMD 3498)

White solid: mp 194-197° C. (dec); $^1$H NMR (D$_2$O) δ 1.93-2.12 (m, 4H), 2.42 (s, 3H), 3.25 (s, 8H), 3.48 (s, 8H), 4.28 (s, 2H), 4.30 (s, 2H), 4.33 (s, 2H), 7.44 (s, 4H), 8.33 (s, 1H), 8.46 (s, 1H); $^{13}$C NMR (D$_2$O) δ 18.01, 18.72, 19.80, 36.66, 37.05, 37.13, 40.70, 40.89, 41.27, 43.99, 47.47, 48.14, 50.61, 59.06, 129.97, 131.43, 132.04, 132.99, 140.93, 144.98, 146.49, 153.51; FAB MS m/z 509 (M+H$^{81}$Br, 17), 507 (M+H$^{79}$Br, 15), 426 (M+H, 100), 320 (21), 247 (20). Anal. (C$_{24}$H$_{39}$N$_7$.5.5HBr); Calc. C, 33.10; H, 5.15; N, 11.26; Br, 50.47. Found C, 32.80; H, 5.41; N, 11.00; Br, 50.58.

EXAMPLE 6

N-[1,4,8,11-Tetraazacyclotetradecanyl-1,4-phenylenebis(methylene)]-2-(amino-ethyl)pyridine hexahydrobromide (AMD 3497)

White solid: mp 195-198° C. (dec); $^1$H NMR (D$_2$O) δ 1.98-2.17 (m, 4H), 3.20-3.38 (m, 8H), 3.38-3.63 (m, 12H), 4.27 (s, 2H), 4.39 (s, 2H), 7.50 (s, 4H), 7.80-7.89 (m, 2H), 8.42 (m, 1H), 8.58 (d, 1H, J=5.8 Hz); $^{13}$C NMR (D$_2$O) δ 18.51, 19.14, 29.85, 37.56 (3C), 41.21, 41.41, 41.82, 44.57, 45.27, 47.83, 51.10, 58.74, 126.35, 127.93, 130.66, 131.27, 131.99, 132.69, 141.89, 147.79, 150.91; FAB MS m/z 507 (M+H$^{81}$Br, 40), 505 (M+H$^{79}$Br, 34), 425 (M+H, 100). Anal. (C$_{25}$H$_{40}$N$_6$.6HBr); Calc. C, 32.99; H, 5.09; N, 9.23; Br, 52.67. Found C, 32.79; H, 5.34; N, 9.11; Br, 52.45.

EXAMPLE 7

N-[1,4,8,11-Tetraazacyclotetradecanyl-1,4-phenylenebis(methylene)]-2-(amino-methyl)thoiphene pentahydrobromide (AMD 3516)

White solid: mp 245-248° C. (dec); $^1$H NMR (D$_2$O) δ 1.87-2.12 (m, 4H), 3.02-3.51 (m, 16H), 4.17 (s, 4H), 4.38 (s, 2H), 6.97 (t, 1H, J=3.9 Hz), 7.13 (d, 1H, J=3.1 Hz), 7.41 (s, 5H); $^{13}$C NMR (D$_2$O) δ 18.80, 19.52, 38.03, (3C), 41.59 (2C), 42.21, 44.89 (2C), 48.15, 49.83, 58.52, 128.13, 129.12, 131.15, 131.47, 131.50, 131.90, 132.42, 132.87; FAB MS m/z 498 (M+H$^{81}$Br, 11), 496 (M+H$^{79}$Br, 9), 416 (M+H, 53), 218 (100), 201 (64). Anal. (C$_{23}$H$_{37}$N$_5$S.5HBr); Calc. C, 33.68; H, 5.16; N, 8.54; Br, 48.71. Found C, 33.85; H, 5.22; N, 8.50; Br, 48.52.

EXAMPLE 8

N-[1,4,8,11-Tetraazacyclotetradecanyl-1,4-phenylenebis(methylene)]-2-(amino-ethyl)mercaptan pentahydrobromide dihydrate (AMD 3530)

White solid: mp 234-236° C. (dec); $^1$H NMR (D$_2$O) δ 1.75-2.05 (m, 4H), 2.75-3.45 (m, 20H), 4.05 (s, 2H), 4.15 (s, 2H), 7.35 (s, 4H); FAB MS m/z 462 (MH+H$^{81}$Br, 15), 460 (MH+H$^{79}$Br, 15), 380 (M+H, 100), 300 (64), 279 (47), 239 (49). Anal. (C$_{20}$H$_{37}$N$_5$S.5HBr.2H$_2$O.0.5HOAc) requires C, 29.67; H, 5.69; N, 8.24; Br, 46.99. Found C, 29.31; H, 5.72; N, 8.25; Br, 46.64.

EXAMPLE 9

N-[1,4,8,11-Tetraazacyclotetradecanyl-1,4-phenylenebis(methylene)]-2-amino-benzylamine pentahydrobromide (AMD 3517)

White solid: mp 203-206° C. (dec); $^1$H NMR (D$_2$O) δ 1.85-2.13 (m, 4H), 3.02-3.58 (m, 16H), 4.23 (s, 2H), 4.31 (s, 4H), 7.23-7.54 (m, 8H); $^{13}$C NMR (D$_2$O) δ 18.03, 19.29, 37.78 (3C), 41.37 (2C), 42.00, 44.82, 46.25, 47.96, 51.16, 58.68, 124.04, 124.40, 129.40, 130.75, 131.21 (2C), 131.88, 131.96, 132.46, 132.83; FAB MS m/z 507 (M+H$^{81}$Br, 15), 505 (M+H$^{79}$Br, 18), 425 (M+H, 100), 320 (30), 201 (51). Anal. (C$_{25}$H$_{40}$N$_6$.5.75HBr.0.5H$_2$O). Calc. C, 33.42; H, 5.19; N, 9.35; Br, 51.14. Found C, 33.69; H, 5.35; N, 9.00; Br, 51.13.

EXAMPLE 10

N-[1,4,8,11-Tetraazacyclotetradecanyl-1,4-phenylenebis(methylene)]-4-amino-benzylamine hexahydrobromide (AMD 3544)

Yellow solid: mp 120-125° C. (dec); $^1$H NMR (D$_2$O) δ 1.8-2.0 (m, 4H), 2.9-3.4 (m, 16H), 4.1 (s, 2H), 4.18 (s, 4H), 7.2-7.5 (m, 8H); $^{13}$C NMR (D$_2$O) δ 18.86, 19.57, 38.14, 41.76, 43.74, 45.14, 48.24, 50.14, 50.42, 51.49, 58.38, 124.13, 131.13, 131.30, 131.83, 131.92, 131.96, 132.67; FAB MS m/z 507 (M+H$^{81}$Br, 5), 505 (M+H$^{79}$Br, 5), 425 (M+H, 45), 201 (47), 155 (75), 106 (100). Anal. (C$_{25}$H$_{40}$N$_6$.6HBr.HOAc) requires C, 33.43; H, 5.19; N, 8.66; Br, 49.42; O, 3.30. Found C, 33.42; H, 5.49; N, 8.62; Br, 49.23.

EXAMPLE 11

N-[1,4,8,11-Tetraazacyclotetradecanyl-1,4-phenylenebis(methylene)]-4-(amino-ethyl)imidazole hexahydrobromide (AMD 3543)

Off white solid: mp 135-140° C. (dec); $^1$H NMR (D$_2$O) δ 1.75 (m, 2H), 190 (m, 2H), 2.70-3.27 (m, 20H), 3.77 (s, 2H), 4.14 (s, 2H), 7.18 (s, 1H), 7.25 (d, 2H, J=7.97 Hz), 7.37 (d, 2H, J=7.97 Hz), 8.48 (s, 1H); FAB MS m/z 496 (M+H$^{81}$Br, 5), 494 (M+H$^{79}$Br, 5), 414 (M+H, 17), 201 (15). Anal. (C$_{23}$H$_{39}$N$_7$.6HBr) requires C, 30.73; H, 5.04; N, 10.91; Br, 53.32. Found C, 30.39; H, 5.41; N, 10.41; Br, 53.66.

EXAMPLE 12

N-[1,4,8,11-Tetraazacyclotetradecanyl-1,4-phenylenebis(methylene)]-benzylamine pentahydrobromide (AMD 3529)

Off white solid: mp 245-250° C. (dec); $^1$H NMR (D$_2$O) δ 1.9-2.1 (m, 4H), 3.2-3.6 (m, 16H), 4.12 (s, 2H), 4.15 (s, 2H), 4.36 (s, 2H), 7.30 (s, 5H), 7.41 (d, 2H, J=8.3 Hz) 7.46 (d, 2H, J=8.3 Hz); $^{13}$C NMR (D$_2$O) δ 18.43, 19.06, 37.29, 37.46, 37.63, 41.09, 41.32, 41.68, 44.46, 47.74, 50.18, 51.00, 58.79, 129.53, 129.97, 130.18, 130.35, 130.68, 131.18, 131.92, 133.14; FAB MS m/z 492 (M+H$^{81}$Br, 13), 490 (M+H$^{79}$Br, 13), 410 (M+H, 100), 201 (36). Anal. (C$_{25}$H$_{39}$N$_5$.5HBr); requires C, 36.88; H, 5.45; N, 8.60; Br, 49.07. Found C, 36.79; H, 5.56; N, 8.48; Br, 48.79.

The compounds of the invention were tested in a screen by the MTT method (*J. Virol. Methods* 120: 309-321 (1988)). MT-4 cells (2.5×10$^4$/well) were challenged with HIV-1 (HTLV-IIIB) or HIV-2 (LAV-2 ROD) at a concentration of 100 CCID$_{50}$ and incubated in the presence of various concentrations of the test compounds, which were added immediately after challenge with the virus. After 5 days culture at 37° C. in a CO$_2$ incubator, the number of viable cells was assessed by the MTT (tetrazolium) method. Antiviral activity and cytotoxicity of the compounds are expressed in Table 1 below as EC$_{50}$ (μg/ml) and CC$_{50}$ (μg/ml), respectively. The potential therapeutic usefulness was assessed by calculating a Selectivity Index (SI) corresponding to the ratio of CC$_{50}$ to EC$_{50}$.

TABLE 1

| | Anti-HIV activity data | | | |
|---|---|---|---|---|
| | CC$_{50}$ | EC$_{50}$ (μg/mL) | | SI |
| Compound | (μg/mL) | HIV-1 (IIIB) | HIV-2 | HIV-1 |
| 1 AMD3465 | >250 | 0.008 | 0.032 | 3 × 10$^4$ |
| 2 AMD3538 | 209 | 0.1 | 6.7 | 2.0 × 10$^3$ |
| 3 AMD3500 | >250 | 0.6 | 10.3 | 417 |
| 4 AMD3499 | >250 | 1.8 | 28.5 | 138 |
| 5 AMD3498 | >250 | 0.2 | 7.1 | 1.2 × 10$^3$ |
| 6 AMD3497 | >250 | 1.8 | 3.8 | 138 |
| 7 AMD3516 | 158 | 0.7 | 9.8 | 225 |
| 8 AMD3530 | 175 | 0.5 | 2.0 | 350 |
| 9 AMD3517 | 153 | 0.8 | 10.6 | 191 |
| 10 AMD3544 | 222 | 0.7 | 3.7 | 317 |
| 11 AMD3543 | 239 | 0.2 | 1.0 | 1 × 10$^3$ |
| 12 AMD3529 | 130 | 0.4 | 2.6 | 325 |

In this field of study, it is considered that any compound exhibiting a Selectivity Index of greater than 100 has the considerable potential for further study. HIV is one of the most challenging viruses to combat, and the results given above provide an indication of activity against other retroviruses and against other viruses in general.

EXAMPLE 13

N-[4-(1,4,7-Triazacyclotetra-decanyl)-1,4-phenylenebis(methylene)]-2-(aminomethyl)pyridine (AMD 7049)

N,N'-Bis(2-Nitrobenzenesulfonyl)-1,7-heptanediamine

To a stirred solution of 1,7-heptanediamine (5.01 g, 38.5 mmol) and Et$_3$N (13.5 mL, 96.9 mmol) in CH$_2$Cl$_2$ (70 mL) was added a solution of 2-nitrobenzenesulfonyl chloride (18.80 g, 84.83 mmol) in CH$_2$Cl$_2$ (40 mL). The mixture was stirred at room temperature under nitrogen for 72 h and then concentrated in vacuo. The residue was stirred in diethyl ether (100 mL), and the precipitate was collected by filtration and washed with H$_2$O (300 mL) followed by diethyl ether (300 mL) to give a gray solid (18.5 g, 96%): $^1$H NMR (DMF-d$_7$) δ 1.21 (m, 6H), 1.49 (m, 4H), 3.04 (m, 4H), 7.87 (m, 2H), 7.95 (m, 4H), 8.04 (m, 2H), 8.15 (m, 2H).

General Procedure D

4-Diethoxyphosphoryl-1,7-bis(2-nitrobenzenesulfonyl)-1,4,7-triazacyclotetradecane To a stirred solution of N,N'-bis(2-nitrobenzenesulfonyl)-1,7-heptanediamine (9.00 g, 18.0 mmol) and Cs$_2$CO$_3$ (17.8 g, 54.6 mmol) in DMF (500 mL) under nitrogen maintained at 80° C. was added dropwise a solution of N-(diethoxyphosphoryl)-O,O'-bis(2-methylsulfonyl)di-ethanolamine (Bridger et al., J. Med. Chem. 1995, 38, 366-378) (7.95 g, 20.0 mmol) in DMF (50 mL) over 8 h. Heating was continued for a further 17 h and the mixture was then allowed to cool and concentrated in vacuo. The residue was partitioned between $CHCl_3$ (140 mL) and $H_2O$ (80 mL) and the aqueous layer was separated and extracted with $CHCl_3$ (3×40 mL). The combined organic extracts were dried ($MgSO_4$) and concentrated in vacuo and the residue was purified by column chromatography on silica gel (ethylacetate) to give the desired macrocycle as a yellow crystalline solid (2.85 g, contaminated with DMF).

To remove the unwanted DMF impurity, the residue was dissolved in EtOAc (75 mL), and the solution was washed sequentially with 5% $NaHCO_3$ (2×10 mL) and brine (5×10 mL), dried ($MgSO_4$) and evaporated to give a yellow amorphous solid (2.52 g, 20%): $^1H$ NMR ($CDCl_3$) δ 1.32 (t, 6H, J=7.1 Hz), 1.51 (m, 6H), 1.61 (m, 4H), 3.33 (m, 12H), 4.03 (m, 4H), 7.61 (m, 2H), 7.71 (m, 4H), 8.03 (m, 2H).

General Procedure E

Synthesis of 1,7-Bis(2-nitrobenzenesulfonyl)-1,4,7-triazacyclotetradecane

To a stirred suspension of the macrocycle from above (1.88 g, 2.66 mmol) in acetic acid (5 mL) was added a freshly prepared solution of saturated HBr(g) in acetic acid (20 mL) and the resulting homogeneous solution was stirred at room temperature for a further 22 h. Addition of diethyl ether (250 mL) to the reaction mixture gave a precipitate that was allowed to settle to the bottom of the flask and the supernatant solution was decanted. The precipitate was washed with ether by decantation (repeated 3×) and the residue was then partitioned between $CH_2Cl_2$ (40 mL) and 1N aqueous NaOH (25 mL). The separated aqueous layer was extracted with $CH_2Cl_2$ (2×20 mL) and the combined organic extracts were washed with brine (20 mL), then dried ($MgSO_4$) and concentrated in vacuo to give a yellow amorphous solid (1.23 g, 81%): $^1H$ NMR ($CDCl_3$) δ 1.46-1.67 (m, 10H), 2.90 (m, 4H), 3.34 (m, 8H), 7.61 (m, 2H), 7.70 (m, 4H), 7.97 (m, 2H).

4-Bromomethylbenzyl Alcohol

To a solution of methyl 4-bromomethylbenzoate (5.73 g, 25 mmol) in dry $CH_2Cl_2$ (150 mL) cooled to −78° C. with stirring under nitrogen was added dropwise a solution of DIBAL-H (82.5 mL, 1.0 M solution in THF). Stirring was continued for 1.5 h at −78° C., and the reaction mixture was then allowed to warm to 0° C. and quenched with $H_2O$. The organic layer was separated and the aqueous was extracted with $CH_2Cl_2$ (2×100 mL). The combined organic extracts were dried ($MgSO_4$) and evaporated to give the desired alcohol (5.0 g, 100%) as a white solid: $^1H$ NMR ($CDCl_3$) δ 1.84 (br, 1H), 4.49 (s, 2H), 4.67 (s, 2H), 7.33 (d, 2H, J=8.2 Hz), 7.38 (d, 2H, J=8.2 Hz).

N-(2-Nitrobenzenesulfonyl)-2-(aminomethyl)pyridine

A solution of 2-nitrobenzenesulfonylchloride (16.62 g, 0.075 mol) in dry $CH_2Cl_2$ (120 mL) was added dropwise via cannula to a stirred solution of 2-(aminomethyl)pyridine (5.41 g, 0.05 mol) and $Et_3N$ (13.9 mL, 0.10 mol) in dry $CH_2Cl_2$ (150 mL) under nitrogen. The reaction mixture was stirred for three hours at room temperature, and then quenched with water (20 mL). The aqueous layer was separated and extracted with EtOAc (5×80 mL). The combined organic extracts were dried ($MgSO_4$) and evaporated to small volume to give a white precipitate which was collected by filtration and washed with cold $CH_2Cl_2$ to give the desired product (11.37 g, 78%) as a white solid: $^1H$ NMR (Acetone-$d_6$) δ 4.46 (s, 2H), 7.19 (dd, 1H, J=7.4, 4.5 Hz), 7.25-7.35 (br s, 1H), 7.39 (d, 1H, J=7.7 Hz), 7.68 (ddd, 1H, J=7.7, 7.5, 1.8 Hz), 7.76-7.88 (m, 2H), 7.94 (dd, 1H, J=7.7, 1.5 Hz), 8.04 (dd, 1H, J=7.5, 1.8 Hz), 8.38 (d, 1H, J=4.5 Hz).

N-[1-Methylene-4-(hydroxymethylene)phenylene]-N-(2-Nitrobenzenesulfonyl)-2-(aminomethyl)pyridine A mixture of N-(2-nitrobenzenesulfonyl)-2-(aminomethyl)pyridine (5.87 g, 20 mmol), 4-bromomethylbenzyl alcohol (4.02 g, 20 mmol) and $K_2CO_3$ (5.53 g, 40 mmol) in dry $CH_3CN$ (150 mL) were heated at 60° C. for 4 h with stirring under nitrogen. The mixture was then allowed to cool to room temperature, the solvent evaporated and the residue was partitioned between water and $CH_2Cl_2$. The separated aqueous phase was extracted with $CH_2Cl_2$, and the combined organic extracts were dried ($MgSO_4$) and evaporated. The residue was suspended in ethyl acetate/hexane (1:1) and collected by filtration to give the desired product (6.87 g, 83%) as a white solid: $^1H$ NMR ($CDCl_3$) δ 1.78 (t, 1H, J=5.8 Hz), 4.58 (s, 2H) 4.60 (s, 2H), 4.64 (d, 2H, J=5.8 Hz), 7.13-7.26 (m, 6H), 7.54-7.59 (m, 2H), 7.66-7.68 (m, 2H), 7.98 (d, 1H, J=7.4 Hz), 8.40 (d, 1H, J=3.8 Hz).

N-[1-Methylene-4-(chloromethylene)phenylene]-N-(2-Nitrobenzenesulfonyl)-2-(aminomethyl)pyridine To a stirred solution of the alcohol from above (1.91 g, 4.62 mmol) and $Et_3N$ (2.0 mL, 14 mmol) in $CH_2Cl_2$ (20 mL) cooled in an ice bath under nitrogen, was added methanesulfonyl chloride (0.73 mL, 9.4 mmol) and the reaction mixture was then heated to reflux for a further 6 h. The solution was diluted with $CH_2Cl_2$ (60 mL) and washed with 10% aqueous HCl (2×20 mL), 5% aqueous $NaHCO_3$ (20 mL), and $H_2O$ (25 mL) then dried ($MgSO_4$) and concentrated in vacuo to give an orange oil (1.95 g, 98%): $^1H$ NMR ($CDCl_3$) δ 4.52 (s, 2H), 4.60 (s, 4H), 7.12-7.26 (m, 6H), 7.55 (m, 2H), 7.67 (d, 2H, J=4.0 Hz), 7.94 (d, 1H, J=8.0 Hz), 8.41 (d, 1H, J=4.8 Hz). This was used without further purification.

General Procedure F

N-[4-[1,7-Bis(2-nitrobenzenesulfonyl)-1,4,7-triazacyclotetra-decanyl]-1,4-phenylenebis(methylene)]-N-(2-Nitrobenzenesulfonyl)-2-(aminomethyl)pyridine A mixture of 1,7-bis(2-nitrobenzenesulfonyl)-1,4,7-triazacyclotetradecane (1.1 g, 1.9 mmol), the chloride from above (0.98 g, 2.3 mmol) and $K_2CO_3$ (0.85 g, 6.2 mmol) were heated to reflux in $CH_3CN$ (30 mL) under nitrogen for 62 h. The solvent was evaporated in vacuo and the residue was partitioned between $CH_2Cl_2$ (100 mL) and brine (70 mL). The aqueous phase was separated and extracted with $CH_2Cl_2$ (40 mL) and the combined organic extracts were dried ($MgSO_4$) and concentrated in vacuo. The residue was purified by column chromatography on silica gel (3% $MeOH/CH_2Cl_2$) and the evaporated fractions containing the desired product were subjected to a second column purification on silica gel (ethyl acetate) to give a pale yellow amorphous solid (940 mg, 49%): $^1H$ NMR ($CDCl_3$) δ 1.44 (br s, 6H), 1.60 (br s, 4H), 2.75 (m, 4H), 3.23-3.33 (m, 8H), 3.59 (s, 2H), 4.58 (s, 2H), 4.59 (s, 2H), 7.08-7.20 (m, 6H), 7.55-7.70 (m, 10H), 7.82 (dd, 2H, J=7.6, 1.6 Hz), 7.99 (d, 1H, J=7.8 Hz), 8.40 (d, 1H, J=4.7 Hz).

N-[4-(1,4,7-Triazacyclotetra-decanyl)-1,4-phenylenebis(methylene)]-2-(aminomethyl)pyridine Pentahydrobromide Dihydrate The intermediate from above (870 mg, 0.90 mmol), $K_2CO_3$ (1.15 g, 8.32 mmol), and thiophenol (0.33 mL, 3.2 mmol) were stirred in DMF (12 mL) for 7.5 h at room temperature. The mixture was concentrated in vacuo and the residue was partitioned between $CH_2Cl_2$ (30 mL) and $H_2O$ (15 mL). The organic phase was separated, washed with 5% $NaHCO_3$ (10 mL) then $H_2O$ (10 mL) then dried ($MgSO_4$) and concentrated in vacuo. The yellow residue was purified by column chromatography on basic alumina ($CH_2Cl_2$, 1% $MeOH/CH_2Cl_2$, and 10% $MeOH/CH_2Cl_2$) to give the free base as a yellow oil (134 mg, 36%): $^1$H NMR ($CDCl_3$) δ 1.48 (br s, 6H), 1.60 (br s, 4H), 2.61 (m, 12H), 3.56 (s, 2H), 3.83 (s, 2H), 3.92 (s, 2H), 7.16 (m, 1H), 7.24 (m, 2H), 7.32 (m, 3H), 7.79 (m, 1H), 8.56 (d, 1H, J=4.7 Hz).

The free base (134 mg, 0.33 mmol) was dissolved in EtOH (4 mL) and a freshly prepared solution of saturated HBr(g) in EtOH (9 mL) was added, giving a white precipitate. The mixture was stirred for 5 min and diethyl ether (15 mL) was added. The precipitate was allowed to settle to the bottom of the flask and the supernatant solution was decanted. The solid was then dissolved in MeOH (5 mL) and re-precipitated with a large volume of ether, washed with ether by decantation (15×) and finally, the last traces of ether were removed via evaporation at reduced pressure (room temperature). Drying the solid in vacuo at 40° C. for 16 h, gave the desired product as a white solid (178 mg, 63%): $^1$H NMR (DMSO-$d_6$) δ 1.44 (br s, 6H), 1.75 (br s, 4H), 3.04 (br s, 8H), 3.37 (m, 4H), 4.06 (br s, 2H), 4.31 (s, 2H), 4.38 (s, 2H), 7.52-7.68 (m, 6H), 8.01 (m, 1H), 8.70 (d, 1H, J=5.0 Hz); FAB-MS m/z 492 (MH+ $H^{81}Br$), 490 (MH+$H^{79}Br$), 410 (M+H). Anal. Calcd for $C_{25}H_{39}N_5$.5HBr0.1Et$_2$O2.3H$_2$O: C, 35.35; H, 5.79; N, 8.11; Br, 46.29. Found: C, 35.55; H, 5.70; N, 8.18; Br, 46.17.

EXAMPLE 14

N-[7-(4,7,10,17-Tetraazabicyclo[13.3.1]heptadeca-1 (17),13,15-trienyl)-1,4-phenylenebis(methylene)]-2-(aminomethyl)pyridine (AMD 7050)

2,6-Bis(2-aminoethyl)pyridine was prepared as described in Bridger et al. U.S. Pat. No. 5,698,546, which is hereby incorporated in its entirety by reference herein.

2,6-Bis[N-(2-nitrobenzenesulfonyl)-2-aminoethyl] pyridine

To a stirred solution of 2,6-Bis(2-aminoethyl)pyridine (2.7 g, 16 mmol) and $Et_3N$ (5.7 mL, 41 mmol) in $CH_2Cl_2$ (35 mL) was added 2-nitrobenzenesulfonyl chloride (8.01 g, 36.1 mmol) in $CH_2Cl_2$ (20 mL) and the mixture was stirred at room temperature under nitrogen for 42 h. The mixture was washed with brine (25 mL) and the organic phase was dried ($MgSO_4$) and concentrated in vacuo. The brown residue was purified by column chromatography on silica gel (50% then 60% THF/hexane) to give a pale yellow solid (5.2 g, 59%): $^1$H NMR ($CDCl_3$) δ 3.01 (m, 4H), 3.52 (m, 4H), 6.38 (m, 2H), 6.94 (d, 2H, J=7.7, Hz), 7.47 (t, 1H, J=7.7 Hz), 7.72 (m, 4H), 7.82 (m, 2H), 8.13 (m, 2H).

7-Diethoxyphosphoryl-4,10-Bis(2-nitrobenzenesulfonyl)-4,7,10,17-tetraazabicyclo[13.3.1]heptadeca-1(17),13,15-triene Using General Procedure D: Reaction of 2,6-bis[N-(2-nitrobenzenesulfonyl)-2-aminoethyl]pyridine (5.2 g, 9.7 mmol) and N-(diethoxyphosphoryl)-O,O'-bis(2-methylsulfonyl)di-ethanolamine (4.25 g, 10.7 mmol) followed by silica gel column purification (60% then 90% THF/hexane) of the reaction products gave the title compound as a yellow amorphous solid (1.48 g, 21%): $^1$H NMR ($CDCl_3$) δ 1.23 (t, 6H, J=7.1 Hz), 2.60 (m, 4H), 2.98-3.08 (m, 8H), 3.84-3.94 (m, 8H), 7.11 (d, 2H, J=7.6 Hz), 7.56-7.74 (m, 7H), 8.07 (m, 2H).

4,10-Bis(2-nitrobenzenesulfonyl)-4,7,10,17-tetraazabicyclo[13.3.1]heptadeca-1(17),13,15-triene Using General Procedure E: Reaction of 7-diethoxyphosphoryl-4,10-bis(2-nitrobenzenesulfonyl)-4,7,10,17-tetraazabicyclo[13.3.1]heptadeca-1(17),13,15-triene (1.04 g, 1.4 mmol) gave the title compound as a yellow amorphous solid (744 mg, 88%): $^1$H NMR ($CDCl_3$) δ 2.81 (m, 4H), 3.08 (m, 4H), 3.33 (m, 4H), 3.88 (m, 4H), 7.07 (d, 2H, J=7.7 Hz), 7.54-7.71 (m, 7H), 8.02 (m, 2H).

N-[7-[4,10-Bis(2-nitrobenzenesulfonyl)-4,7,10,17-tetraazabicyclo[13.3.1]heptadeca-1(17),13,15-trienyl]-1,4-phenylenebis(methylene)]-N-(2-nitrobenzenesulfonyl)-2-(aminomethyl)pyridine Using General Procedure F: Reaction of 4,10-bis(2-nitrobenzenesulfonyl)-4,7,10,17-tetraazabicyclo[13.3.1]heptadeca-1(17),13,15-triene (740 mg, 1.2 mmol) and N-[1-methylene-4-(chloromethylene)phenylene]-N-(2-nitrobenzenesulfonyl)-2-(aminomethyl)pyridine (610 mg, 1.4 mmol) followed by silica gel column purification (50% then 80% THF/hexane) of the reaction products gave the title compound as a yellow amorphous solid (648 mg, 54%): $^1$H NMR ($CDCl_3$) δ 2.26 (m, 4H), 3.03 (m, 8H), 3.37 (s, 2H), 3.94 (m, 4H), 4.56 (s, 2H), 4.57 (s, 2H), 6.95-7.17 (m, 8H), 7.52-7.72 (m, 11H), 7.85 (m, 2H), 7.98 (d, 1H, J=7.7 Hz), 8.39 (d, 1H, J=4.8 Hz).

General Procedure G

N-[7-(4,7,10,17-Tetraazabicyclo[13.3.1]heptadeca-1 (17),13,15-trienyl)-1,4-phenylenebis(methylene)]-2-(aminomethyl)pyridine Hexahydrobromide Trihydrate To a solution of N-[7-[4,10-bis(2-nitrobenzenesulfonyl)-4, 7,10,17-tetraazabicyclo[13.3.1]heptadeca-1(17),13,15-trienyl]-1,4-phenylenebis(methylene)]-N-(2-nitrobenzenesulfonyl)-2-(aminomethyl)pyridine (640 mg, 0.64 mmol) in DMF (9 mL) containing $K_2CO_3$ (806 mg, 5.83 mmol) was added thiophenol (0.24 mL, 2.3 mmol) and the mixture was stirred at room temperature for 2 h. The mixture was concentrated in vacuo and the residue partitioned between ethyl acetate (30 mL) and water (10 mL). The organic phase was separated and extracted with 5% $NaHCO_3$ (3×5 mL) then brine (5 mL). The combined aqueous phases were extracted with $CH_2Cl_2$ (3×10 mL). The combined organic extracts were dried ($MgSO_4$) and evaporated and the residue was purified by column chromatography on alumina ($CH_2Cl_2$ followed by 10% MeOH/$CH_2Cl_2$) to give the free base of the title compound as a yellow oil (83 mg, 29%): $^1$H NMR ($CDCl_3$) δ 2.57 (m, 8H), 3.01 (s, 8H), 3.36 (s, 2H), 3.78 (s, 2H), 3.92 (s, 2H), 6.64 (d, 2H, J=8.0 Hz), 7.07 (m, 4H), 7.18 (m, 1H), 7.33 (d, 1H, J=7.7 Hz), 7.67 (m, 2H), 8.58 (d, 1H, J=4.8 Hz).

The free base (74 mg, 0.17 mmol) was dissolved in MeOH (3 mL) and a freshly prepared solution of saturated HBr(g) in MeOH (7 mL) was added giving a white precipitate. The mixture was stirred for 5 min and diethyl ether was added (10 mL), the solid was allowed to settle to the bottom of the flask and the supernatant solution decanted. The solid was washed by decantation with MeOH (5×5 mL) then ether (10×5 mL) and the last traces of ether were removed by evaporation in vacuo followed by drying in vacuo at 40° C. for 17.5 h to give the title compound as a white solid (153 mg, 93%): $^1$H NMR (DMSO-$d_6$) δ 2.81 (br s, 4H), 3.28 (m, 8H), 3.61 (br s, 4H), 3.85 (s, 2H), 4.27 (s, 2H), 4.36 (s, 2H), 7.29 (d, 2H, J=7.7 Hz), 7.36 (d, 2H, J=7.7 Hz), 7.53 (m, 3H), 7.63 (d, 1H, J=7.7 Hz), 7.80 (t, 1H, J=7.7 Hz), 7.99 (m, 1H), 8.69 (d, 1H, J=5.3 Hz); FAB-MS m/z 527 (MH+H$^{81}$Br), 525 (MH+H$^{79}$Br), 445 (M+H). Anal. Calcd for $C_{27}H_{36}N_6$.6HBr.3$H_2O$: C, 32.95; H, 4.92; N, 8.54; Br, 48.72. Found: C, 32.75; H, 4.89; N, 8.39; Br, 48.61.

EXAMPLE 15

N-[7-(4,7,10-Triazabicyclo[13.3.1]heptadeca-1(17), 13,15-trienyl)-1,4-phenylenebis(methylene)]-2-(aminomethyl)pyridine (AMD7051)

1,3-Phenylenebis(ethylene)diamine

To a solution of 1,3-phenylenediacetonitrile (9.37 g, 60 mmol) in $CH_3OH$ (saturated with $NH_3$, 150 mL) was added Raney-Ni (ca. 20 g, previously washed with $CH_3OH$ several times) and the mixture was hydrogenated at 45 psi on a Parr apparatus for 48 h. The reaction mixture was filtered through celite and the filtrate evaporated to give the crude product (9.45 g, 96%) as a light green oil: $^1$H NMR (CDCl$_3$) δ 0.80-1.50 (br s, 4H), 2.70-2.76 (m, 4H), 2.94-2.99 (m, 4H), 7.01-7.07 (m, 3H), 7.18-7.26 (m, 1H). This was used in the next step without further purification.

N,N'-Bis(2-Nitrobenzenesulfonyl)-1,3-Phenylenebis (ethylene)diamine

A solution of 2-nitrobenzenesulfonylchloride (19.94 g, 0.090 mol) in dry $CH_2Cl_2$ (70 mL) was added dropwise via cannula to a stirred solution of 1,3-phenylenebis(ethylene) diamine (4.92 g, 0.030 mol) and $Et_3N$ (16.7 mL, 0.12 mol) in dry $CH_2Cl_2$ (80 mL) under nitrogen. The reaction mixture was stirred overnight at room temperature, and then quenched with water (20 mL). The precipitate was collected by filtration and washed with $H_2O$, $CH_3OH$, and $Et_2O$ to give the desired product (9.22 g, 58%) as a white solid: $^1$H NMR (DMSO-$d_6$) δ 2.66 (t, 4H, J=7.7 Hz), 3.08-3.18 (br s, 4H), 6.94 (d, 2H, J=6.4 Hz), 6.98 (s, 1H), 7.12 (dd, 1H, J=6.4, 6.4 Hz), 7.78-7.84 (br m, 4H), 7.90-7.64 (br m, 4H), 8.16 (br s, 2H).

7-Diethoxyphosphoryl-4,10-bis(2-nitrobenzenesulfonyl)-4,7,10-triazabicyclo[13.3.1]heptadeca-1(17),13, 15-triene Using General Procedure D: Reaction of N,N'-bis(2-nitrobenzenesulfonyl)-1,3-phenylenebis(ethylene)diamine (8.74 g, 16.4 mmol) with N-(diethoxyphosphoryl)-O,O'-bis (2-methylsulfonyl)di-ethanolamine (6.50 g, 16.4 mmol) followed by silica gel column purification of the reaction products (1:15:35 $CH_3OH$-$Et_2O$—$CH_2Cl_2$) gave the title compound (4.03 g, 33%) as a yellow foam: $^1$H NMR (CDCl$_3$) δ 1.21 (t, 6H, J=6.4 Hz), 2.39-2.46 (br m, 4H), 2.83-2.97 (br m, 8H), 3.68-3.72 (m, 4H), 3.80-3.92 (m, 4H), 7.16 (d, 2H, J=6.5 Hz), 7.18 (s, 1H), 7.24 (dd, 1H, J=6.5, 6.5 Hz), 7.60-7.74 (m, 6H), 8.04-8.08 (m, 2H).

4,10-Bis(2-nitrobenzenesulfonyl)-4,7,10-triazabicyclo[13.3.1]heptadeca-1(17),13,15-triene Using General Procedure E: Reaction of 7-diethoxyphosphoryl-4,10-bis(2-nitrobenzenesulfonyl)-4,7,10-triazabicyclo[13.3.1]heptadeca-1(17),13,15-triene (1.27 g, 1.72 mmol) followed by silica gel column purification of the reaction products (1:15:25 $CH_3OH$-EtOAc—$CH_2Cl_2$ then 20% $CH_3OH$ in $CH_2Cl_2$) gave the title compound (574 mg, 57%) as a light yellow foam: $^1$H NMR (CDCl$_3$) δ 1.42-1.50 (br, 1H), 2.01 (t, 4H, J=5.4 Hz), 2.90-3.10 (br m, 4H), 3.08 (t, 4H, J=5.4 Hz), 3.56-3.60 (br m, 4H), 7.16 (d, 2H, J=6.8 Hz), 7.31 (dd, 1H, J=6.8, 6.8 Hz), 7.36 (s, 1H), 7.61-7.63 (m, 2H), 7.70-7.73 (m, 4H), 8.01-8.04 (m, 2H).

N-[7-[4,10-Bis(2-nitrobenzenesulfonyl)-4,7,10-triazabicyclo[13.3.1]heptadeca-1(17),13,15-trienyl]-1,4-phenylenebis(methylene)]-N-(2-Nitrobenzenesulfonyl)-2-(aminomethyl)pyridine Using General Procedure F: Reaction of 4,10-bis(2-nitrobenzenesulfonyl)-4,7,10-triazabicyclo[13.3.1]heptadeca-1(17),13,15-triene (420 mg, 0.7 mmol) with N-[1-methylene-4-(chloromethylene)phenylene]-N-(2-nitrobenzenesulfonyl)-2-(aminomethyl)pyridine (302 mg, 0.7 mmol) followed by silica gel column purification of the reaction products (1:3 $Et_2O$—$CH_2Cl_2$) gave the title compound (491 mg, 70%) as a pale yellow solid: $^1$H NMR (CDCl$_3$) δ 1.97-2.02 (br m, 4H), 2.73-2.78 (br m, 4H), 2.90-2.94 (br m, 4H), 3.32 (s, 2H), 3.64-3.67 (br m, 4H), 4.55 (s, 2H), 4.58 (s, 2H), 6.93 (d, 2H, J=8.0 Hz), 7.04 (d, 2H, J=8.0 Hz), 7.09-7.16 (br m, 4H), 7.23 (s, 1H), 7.29 (dd, 1H, J=7.9, 7.9 Hz), 7.51-7.72 (m, 10H), 7.80-7.83 (m, 2H), 7.98 (d, 1H, J=7.8 Hz), 8.39 (m, 1H).

N-[7-(4,7,10-Triazabicyclo[13.3.1]heptadeca-1(17), 13,15-trienyl)-1,4-phenylenebis(methylene)]-2-(aminomethyl)pyridine Pentahydrobromide Dihydrate Using General Procedure G: Reaction of N-[7-[4,10-bis(2-nitrobenzenesulfonyl)-4,7,10-triazabicyclo[13.3.1]heptadeca-1(17),13,15-trienyl]-1,4-phenylenebis(methylene)]-N-(2-nitrobenzenesulfonyl)-2-(aminomethyl)pyridine (380 mg, 0.38 mmol) followed by basic alumina column purification of the reaction products (1:20 $CH_3OH$—$CH_2Cl_2$) gave the free base of the title compound.

Conversion of the free base to the hydrobromide salt using a saturated solution of HBr(g) in $CH_3OH$ followed by drying in vacuo overnight, gave the title compound (110 mg, 34% overall) as a white solid: $^1$H NMR (DMSO-$d_6$) δ 2.80-2.88 (br s, 4H), 3.02-3.06 (br s, 4H), 3.10-3.16 (br s, 4H), 3.38-3.44 (br s, 4H), 3.80-3.86 (br s, 2H), 4.25-4.30 (br s, 2H), 4.33-4.37 (br s, 2H), 7.27-7.32 (br m, 4H), 7.42-7.63 (br m, 6H), 7.96 (dd, 1H, J=7.7, 7.7 Hz), 8.10-8.30 (br s, 3H), 8.69 (d, 1H, J=4.9 Hz), 9.45-9.62 (br s, 2H); FAB-MS m/z 526 (MH+H$^{81}$Br), 524 (MH+H$^{79}$Br), 444 (M+H, 100); Anal. Calcd for $C_{28}H_{42}N_5Br_5$.2$H_2O$: C, 38.03; H, 5.24; N, 7.92; Br, 45.18. Found: C, 38.37; H, 5.28; N, 7.76; Br, 45.36.

EXAMPLE 16

N-[1-(1,4,7-Triazacyclotetra-decanyl)-1,4-phenylenebis(methylene)]-2-(aminomethyl)pyridine (AMD 7059)

General Procedure H

4-Diethoxyphosphoryl-7-(2-nitrobenzenesulfonyl)-1, 4,7-triazacyclotetradecane

To a stirred solution of 4-diethoxyphosphoryl-1,7-bis(2-nitrobenzenesulfonyl)-1,4,7-triazacyclotetradecane (1.32 g, 1.87 mmol) and K$_2$CO$_3$ (654 mg, 4.73 mmol) in DMF (11 mL) under nitrogen was added dropwise a solution of thiophenol (0.15 mL, 1.46 mmol) in DMF (8 mL) over 1 h. The mixture was stirred for an additional 3 h and then concentrated in vacuo. The residue was partitioned between CHCl$_3$ (50 mL) and H$_2$O (25 mL). The aqueous phase was separated and extracted with CHCl$_3$ (3×20 mL) and the combined organic extracts were dried (MgSO$_4$) and concentrated in vacuo. The residue was purified by column chromatography on basic alumina (CHCl$_3$ then 3% MeOH/CHCl$_3$) to give the title compound as a yellow oil (178 mg, 23%): $^1$H NMR (CDCl$_3$) δ 1.31 (t, 6H, J=7.0 Hz), 1.40-1.67 (m, 10H), 2.65 (m, 2H), 2.78 (m, 2H), 3.12 (m, 2H), 3.26-3.37 (m, 4H), 3.48 (m, 2H), 3.97-4.09 (m, 4H), 7.61 (m, 1H), 7.68 (m, 2H), 8.06 (m, 1H).

N-[1-[4-Diethoxyphosphoryl-7-(2-nitrobenzenesulfonyl)-1,4,7-triazacyclotetra-decanyl]-1,4-phenylenebis(methylene)]-N-(2-nitrobenzenesulfonyl)-2-(aminomethyl)pyridine Using General Procedure F: Reaction of 4-diethoxyphosphoryl-7-(2-nitrobenzenesulfonyl)-1,4,7-triazacyclotetradecane (236 mg, 0.453 mmol) and N-[1-methylene-4-(chloromethylene)phenylene]-N-(2-nitrobenzenesulfonyl)-2-(aminomethyl)pyridine (238 mg, 0.551 mmol) followed by silica gel column purification of the reaction products (50% then 80% THF/hexane) gave the title compound as a yellow amorphous solid (305 mg, 73%): $^1$H NMR (CDCl$_3$) δ 1.27 (t, 6H, J=7.1 Hz), 1.43 (br s, 8H), 1.63 (br s, 2H), 2.32 (br s, 2H), 2.55 (m, 2H), 3.13-3.41 (m, 8H), 3.49 (s, 2H), 3.85-4.02 (m, 4H), 4.57 (s, 2H), 4.58 (s, 2H), 7.07-7.22 (m, 6H), 7.51-7.71 (m, 7H), 7.98 (d, 1H, J=7.4 Hz), 8.04 (m, 1H), 8.41 (d, 1H, J=4.0 Hz).

N-[1-[7-(2-Nitrobenzenesulfonyl)-1,4,7-triazaclotetra-decanyl]-1,4-phenylenebis(methylene)]-N-(2-nitrobenzenesulfonyl)-2-(aminomethyl)pyridine Using General Procedure E: Reaction of N-[1-[4-diethoxyphosphoryl-7-(2-nitrobenzenesulfonyl)-1,4,7-triazacyclotetra-decanyl]-1,4-phenylenebis(methylene)]-N-(2-nitrobenzenesulfonyl)-2-(aminomethyl)pyridine (300 mg, 0.328 mmol) gave the title compound as a yellow amorphous solid (214 mg, 84%): $^1$H NMR (CDCl$_3$) δ 1.34-1.44 (m, 8H), 1.69 (br s, 2H), 2.34 (m, 2H), 2.52 (m, 2H), 2.62 (m, 2H), 2.82 (m, 2H), 3.42 (m, 6H), 4.58 (s, 2H), 4.59 (s, 2H), 7.08-7.24 (m, 6H), 7.52-7.71 (m, 7H), 8.01 (m, 2H), 8.42 (d, 1H, J=4.1 Hz).

N-[1-(1,4,7-Triazacyclotetra-decanyl)-1,4-phenylenebis(methylene)]-2-(aminomethyl)pyridine Pentahydrobromide Dihydrate A mixture of N-[1-[7-(2-nitrobenzenesulfonyl)-1,4,7-triazacyclotetra-decanyl]-1,4-phenylenebis(methylene)]-N-(2-nitrobenzenesulfonyl)-2-(aminomethyl)pyridine (209 mg, 0.268 mmol), K$_2$CO$_3$ (298 mg, 2.16 mmol), and thiophenol (0.17 mL, 1.7 mmol) in acetonitrile (3 mL) were heated to 50° C. for 16.5 h. The reaction mixture was diluted with CH$_2$Cl$_2$ (10 mL) and washed with brine (10 mL). The separated aqueous phase was extracted with CH$_2$Cl$_2$ (3×5 mL) and the combined organic extracts were dried (MgSO$_4$) and evaporated. The residue was purified by column chromatography on basic alumina (CHCl$_3$ then 10% MeOH/CHCl$_3$) to give the free base of title compound as a yellow oil (92 mg, 84%): $^1$H NMR (CDCl$_3$) δ 1.21-1.62 (m, 10H), 2.40-2.49 (m, 4H), 2.60 (m, 6H), 2.79 (m, 2H), 3.49 (s, 2H), 3.80 (s, 2H), 3.91 (s, 2H), 7.14 (m, 1H), 7.28 (m, 5H), 7.62 (m, 1H), 8.54 (d, 1H, J=4.4 Hz).
Conversion of the free base (86 mg, 0.21 mmol) to the hydrobromide salt using a saturated solution of HBr(g) in MeOH (See General Procedure G) followed by drying in vacuo at 40° C. for 15.5 h gave the title compound as a white solid (128 mg, 70%): $^1$H NMR (D$_2$O) δ 1.48 (br s, 6H), 1.82 (m, 4H), 3.22-3.36 (m, 10H), 3.50 (br s, 2H), 4.48 (s, 4H), 4.64 (s, 2H), 7.62 (s, 4H), 7.88 (m, 1H), 7.94 (d, 1H, J=8.0 Hz), 8.38 (m, 1H), 8.77 (d, 1H, J=5.2 Hz); FAB-MS m/z 492 (MH+H$^{81}$Br), 490 (M+H$^{79}$Br), 410 (M+H). Anal. Calcd for C$_{25}$H$_{39}$N$_5$.5HBr.2.5H$_2$O.0.1Et$_2$O: C, 35.20; H, 5.82; N, 8.08; Br, 46.10. Found: C, 35.48; H, 5.66; N, 8.10; Br, 46.05.

EXAMPLE 17

N-[4-[4,7,10,17-Tetraazabicyclo[13.3.1]heptadeca-1(17),13,15-trienyl]-1,4-phenylenebis(methylene)]-2-(aminomethyl)pyridine (AMD 7063)

7-Diethoxyphosphoryl-10-(2-nitrobenzenesulfonyl)-4,7,10,17-tetraazabicyclo[13.3.1]heptadeca-1(17),13,15-triene Using General Procedure H: Reaction of 7-diethoxyphosphoryl-4,10-bis(2-nitrobenzenesulfonyl)-4,7,10,17-tetraazabicyclo[13.3.1]heptadeca-1(17),13,15-triene (1.48 g, 2.00 mmol) with thiophenol (with an additional heating of the reaction mixture to 50° C. for 1.5 h after the addition) followed by silica gel column purification of the reaction products (8% MeOH/CHCl$_3$) gave the title compound as a light yellow oil (423 mg, 52%): $^1$H NMR (CDCl$_3$) δ 1.23 (t, 6H, J=7.0 Hz), 2.50 (br s, 2H), 2.79 (br s, 2H), 3.02-3.15 (m, 10H), 3.82-3.98 (m, 6H), 7.06 (d, 2H, J=7.6 Hz), 7.54-7.63 (m, 2H), 7.70 (m, 2H), 8.01 (br s, 1H).

N-[4-[7-Diethoxyphosphoryl-10-(2-nitrobenzenesulfonyl)-4,7,10,17-tetraazabicyclo[13.3.1]heptadeca-1(17),13,15-trienyl]-1,4-phenylenebis(methylene)]-N-(2-nitrobenzenesulfonyl)-2-(aminomethyl)pyridine Using General Procedure F: Reaction of 7-diethoxyphosphoryl-10-(2-nitrobenzenesulfonyl)-4,7,10,17-tetraazabicyclo[13.3.1]heptadeca-1(17),13,15-triene (410 mg, 0.738 mmol) and N-[1-methylene-4-(chloromethylene)phenylene]-N-(2-nitrobenzenesulfonyl)-2-(aminomethyl)pyridine (397 mg, 0.919 mmol) followed by silica gel column purification of the reaction products (50%, 80%, and 90% THF/hexane) gave the title compound as a white amorphous solid (441 mg, 63%): $^1$H NMR (CDCl$_3$) δ 1.15 (t, 6H, J=7.0 Hz), 2.42 (m, 4H), 2.77 (m, 2H), 2.92-3.02 (m, 6H), 3.10 (m, 2H), 3.59 (s, 2H), 3.66-3.91 (m, 6H), 4.58 (s, 2H), 4.59 (s, 2H), 6.94 (d, 1H, J=7.6 Hz), 7.07-7.14 (m, 6H), 7.22 (d, 1H, J=7.8 Hz), 7.51-7.72 (m, 8H), 8.00 (d, 1H, J=7.8 Hz), 8.04 (m, 1H), 8.42 (d, 1H, J=4.0 Hz).

N-[4-[7-Diethoxyphosphoryl-4,7,10,17-tetraazabicyclo[13.3.1]heptadeca-1(17),13,15-trienyl]-1,4-phenylenebis(methylene)]-N-2-(aminomethyl)pyridine A mixture of N-[4-[7-diethoxyphosphoryl-10-(2-nitrobenzenesulfonyl)-4,7,10,17-tetraazabicyclo[13.3.1]heptadeca-1(17),13,15-trienyl]-1,4-phenylenebis(methylene)]-N-(2-nitrobenzenesulfonyl)-2-(aminomethyl)pyridine (434 mg, 0.456 mmol), K$_2$CO$_3$ (508 mg, 3.68 mmol), and thiophenol (0.28 mL, 2.7 mmol) were heated to 50° C. in CH$_3$CN (3.5 mL) under nitrogen for 15 h. Upon cooling, the reaction mixture was partitioned between CHCl$_3$ (15 mL) and brine (15 mL) and the aqueous layer was separated and extracted with CHCl$_3$ (3×5 mL). The combined organic extracts were dried (MgSO$_4$) and concentrated in vacuo and the residue was purified by column chromatography on basic alumina (CHCl₃ then 10% MeOH/CHCl₃) to give a yellow oil (218 mg, 82%): ¹H NMR (CDCl₃) δ 1.16 (t, 6H, J=7.1 Hz), 2.35 (m, 2H), 2.55 (m, 2H), 2.75 (m, 2H), 2.82 (m, 2H), 2.96-3.08 (m, 6H), 3.16 (m, 2H), 3.68 (s, 2H), 3.69-3.88 (m, 4H), 3.82 (s, 2H), 3.93 (s, 2H), 6.95 (d, 1H, J=7.6 Hz), 7.00 (d, 1H, J=7.5 Hz), 7.15-7.34 (m, 6H), 7.50 (m, 1H), 7.65 (m, 1H), 8.56 (d, 1H, J=4.7 Hz).

N-[4-[4,7,10,17-Tetraazabicyclo[13.3.1]heptadeca-1 (17),13,15-trienyl]-1,4-phenylenebis(methylene)]-2-(aminomethyl)pyridine Hexahydrobromide Hydrate To a stirred solution of N-[4-[7-diethoxyphosphoryl-4,7,10,17-tetraazabicyclo[13.3.1]heptadeca-1(17),13,15-trienyl]-1,4-phenylenebis(methylene)]-N-2-(aminomethyl)pyridine (211 mg, 0.36 mmol) in acetic acid (0.6 mL) was added a freshly prepared solution of saturated HBr(g) in acetic acid (6 mL) and the reaction mixture was allowed to stir at room temperature for 4 h. Addition of diethyl ether (10 mL) gave a white precipitate that was allowed to settle to the bottom of the flask and the supernatant solution was decanted. The solid was washed by decantation with MeOH (4×5 mL) and ether (6×5 mL) and the remaining traces of ether were removed by evaporation under reduced pressure. The product was dried in vacuo at 40° C. for 17 h, to give the title compound as a pale yellow solid (223 mg, 63%): ¹H NMR (D₂O) δ 3.14-3.36 (m, 10H), 3.55 (m, 4H), 3.75 (m, 2H), 4.45 (s, 2H), 4.50 (s, 2H), 4.64 (s, 2H), 7.22 (m, 2H), 7.53 (s, 4H), 7.70 (m, 1H), 7.95 (m, 1H), 8.00 (d, 1H, J=7.9 Hz), 8.46 (m, 1H), 8.79 (d, 1H, J=3.9 Hz); FAB-MS m/z 527 (MH+H⁸¹Br), 525 (MH+H⁷⁹Br), 445 (M+H). Anal. Calcd for $C_{27}H_{36}N_6 \cdot 6HBr \cdot 1.5H_2O \cdot 0.2Et_2O$: C, 34.35; H, 4.87; N, 8.65; Br, 49.33. Found: C, 34.57; H, 5.04; N, 8.68; Br, 49.09.

EXAMPLE 18

N-[4-[4,7,10-Triazabicyclo[13.3.1]heptadeca-1(17), 13,15-trienyl]-1,4-phenylenebis(methylene)]-2-(aminomethyl)pyridine (AMD7058)

7-Diethoxyphosphoryl-10-(2-nitrobenzenesulfonyl)-4,7,10-triazabicyclo[13.3.1]heptadeca-1(17),13,15-triene Using General Procedure H: Reaction of 7-diethoxyphosphoryl-4,10-bis(2-nitrobenzenesulfonyl)-4,7,10-triazabicyclo[13.3.1]heptadeca-1(17),13,15-triene (1.11 g, 1.5 mmol) followed by silica gel column purification of the reaction products (2:5:20 CH₃OH-Et₂O—CH₂Cl₂ then 1:5 CH₃OH—CH₂Cl₂) gave the title compound as a pale yellow oil (300 mg, 54%): ¹H NMR (CDCl₃) δ 1.21 (t, 6H, J=7.1 Hz), 1.78-1.92 (br s, 1H), 2.31-2.38 (br m, 2H), 2.56-2.60 (br m, 2H), 2.81-2.98 (br m, 10H), 3.60-3.64 (br m, 2H), 3.75-3.91 (m, 4H), 7.05-7.12 (m, 2H), 7.24-7.29 (m, 2H), 7.60-7.63 (m, 1H), 7.68-7.71 (m, 2H), 8.02-8.06 (m, 1H).

N-[4-[7-Diethoxyphosphoryl-10-(2-nitrobenzenesulfonyl)-4,7,10-triazabicyclo[13.3.1]heptadeca-1 (17),13,15-trienyl]-1,4-phenylenebis(methylene)]-N-(2-nitrobenzenesulfonyl)-2-(aminomethyl)pyridine Using General Procedure F: Reaction of 7-diethoxyphosphoryl-10-(2-nitrobenzenesulfonyl)-4,7,10-triazabicyclo [13.3.1]heptadeca-1(17),13,15-triene (290 mg, 0.52 mmol) with N-[1-methylene-4-(chloromethylene)phenylene]-N-(2-nitrobenzenesulfonyl)-2-(aminomethyl)pyridine (271 mg, 0.63 mmol) followed by silica gel column purification of the reaction products (1:12:12 CH₃OH—Et₂O—CH₂Cl₂) gave the title compound (298 mg, 60%) as a pale yellow solid: ¹H NMR (CDCl₃) δ 1.17 (t, 6H, J=7.0 Hz), 2.29-2.45 (br m, 4H), 2.55-2.65 (br m, 2H), 2.71-2.75 (br s, 4H), 2.85-2.91 (br m, 2H), 2.96-2.98 (br m, 2H), 3.57 (s, 2H), 3.67-3.84 (br m, 6H), 4.57-4.61 (br s, 4H), 7.07-7.28 (br m, 10H), 7.55-7.71 (br m, 7H), 7.99-8.02 (m, 2H), 8.42-8.46 (m, 1H).

N-[4-[10-(2-Nitrobenzenesulfonyl)-4,7,10-triazabicyclo[13.3.1]heptadeca-1(17),13,15-trienyl]-1,4-phenylenebis(methylene)]-N-(2-nitrobenzenesulfonyl)-2-(aminomethyl)pyridine Using General Procedure E: Reaction of N-[4-[7-diethoxyphosphoryl-10-(2-nitrobenzenesulfonyl)-4,7,10-triazabicyclo[13.3.1]heptadeca-1(17),13,15-trienyl]-1,4-phenylenebis (methylene)]-N-(2-nitrobenzenesulfonyl)-2-(aminomethyl) pyridine (290 mg, 0.31 mmol) gave the title compound (240 mg, 95%) as a white solid: ¹H NMR (CDCl₃) δ 1.65-1.79 (br s, 1H, coincide with H₂O peak), 2.15-2.19 (br m, 4H), 2.44-2.48 (br m, 2H), 2.61-2.65 (br m, 2H), 2.67-2.71 (br m, 2H), 3.00-3.04 (br m, 2H), 3.10-3.14 (br m, 2H), 3.56-3.60 (br s, 4H), 4.55 (s, 2H), 4.61 (s, 2H), 6.96 (d, 1H, J=7.8 Hz), 7.02-7.10 (br m, 6H), 7.22-7.28 (br m, 3H), 7.52-7.72 (br m, 7H), 7.96-7.99 (m, 2H), 8.42-8.46 (m, 1H). This was used without further purification.

N-[4-[4,7,10-Triazabicyclo[13.3.1]heptadeca-1(17), 13,15-trienyl]-1,4-phenylenebis(methylene)]-2-(aminomethyl)pyridine Pentahydrobromide Dihydrate Using General Procedure G: Reaction of N-[4-[10-(2-nitrobenzenesulfonyl)-4,7,10-triazabicyclo[13.3.1]heptadeca-1(17),13,15-trienyl]-1,4-phenylenebis(methylene)]-N-(2-nitrobenzenesulfonyl)-2-(aminomethyl)pyridine (236 mg, 0.29 mmol) followed by alumina column purification of the reaction products (1:99 CH₃OH—CH₂Cl₂ then 1:10 CH₃OH—CH₂Cl₂) gave the free base of the title compound (111 mg, 86%) as a pale yellow oil: ¹H NMR (CDCl₃) δ 2.24-2.28 (br s, 3H), 2.43-2.50 (br m, 4H), 2.58-2.62 (br m, 2H), 2.73-2.79 (br m, 8H), 2.95-2.98 (br m, 2H), 3.50 (s, 2H), 3.77 (s, 2H), 3.90 (s, 2H), 6.83-6.87 (br m, 3H), 7.05-7.33 (br m, 7H), 7.63-7.67 (m, 1H), 8.54-8.56 (m, 1H).

Conversion of the free base (104 mg, 0.23 mmol) to the hydrobromide salt using a saturated solution of HBr(g) in CH₃OH followed by drying of the product in vacuo, gave the title compound (101 mg, 52%) as a white solid: ¹H NMR (D₂O) δ 2.90-2.94 (br m, 2H), 2.97-3.01 (br m, 2H), 3.12-3.16 (br m, 2H), 3.17-3.21 (br m, 2H), 3.24-3.28 (br m, 4H), 3.47-3.51 (br m, 2H), 3.57-3.61 (br m, 2H), 4.38-4.42 (m, 6H), 7.34-7.40 (m, 2H), 7.46-7.60 (m, 8H), 7.90-7.94 (m, 1H), 8.58-8.62 (m, 1H); FAB-MS m/z 526 (MH+H⁸¹Br), 524 (MH+H⁷⁹Br), 444 (M+H, 100); Anal. Calcd. for $C_{21}H_{42}N_5Br_5 \cdot 2.5H_2O$: C, 37.65; H, 5.30; N, 7.84; Br, 44.73. Found: C, 37.53; H, 5.26; N, 7.79; Br, 44.75.

TABLE 2

| Compound | Inhibition of mAb 12G5 binding IC₅₀[a] (ng/ml) |
|---|---|
| AMD3100 | 27 |
| AMD3465 | 3 |
| AMD7049 | 52 |
| AMD7050 | 1 |
| AMD7051 | 7 |
| AMD7058 | >1000 |
| AMD7059 | >1000 |
| AMD7063 | 9 |
| SDF-1α[b] | 270 |

[a]Inhibition of mAb 12G5 binding to CXCR-4 in SUP-T1 cells.
[b]Natural ligand for CXCR-4 (Bleul et al. Nature, 382: 829-832 (1996); Oberlin et al., Nature, 382: 833-835 (1996)).

TABLE 3

| Compound | % Inhibition of $Ca^{2+}$ flux (conc) or $IC_{50}$[a] (ng/ml) |
|---|---|
| AMD3100 | 5 |
| AMD3465 | 1 |
| AMD7049 | 100% (1 μg/ml) |
| AMD7050 | 100% (1 μg/ml) |
| AMD7051 | 100% (1 μg/ml) |
| AMD7058 | 44% (1 μg/ml) |
| AMD7059 | 36% (1 μg/ml) |
| AMD7063 | 100% (1 μg/ml) |

[a] Inhibition of Signal transduction (increasing intracellular $Ca^{2+}$ flux) induced by SDF-1α binding to CXCR-4 on SUP-T1 cells.

Figure 28:
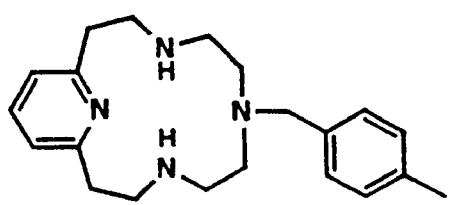
FIG. 28; shows the structural formula of compound AMD 3484.

Each of the following compounds, including AMD 3484 (see FIG. 28), were synthesized according to procedures in Bridger et al., *J. Med. Chem.* 1995, 38, 366-378; *J. Med. Chem.* 1996, 39, 109-119 and U.S. Pat. Nos. 5,583,131, 5,698,546 and 5,817,807, which are each incorporated in their entirety by reference herein.

EXAMPLE 19

1-[2,6-Dimethoxypyrid-4-yl(methylene)]-1,4,8,11-tetraazacyclotetradecane Tetrahydrobromide (AMD 7032)

$^{1}$H NMR ($D_2O$) δ 1.78 (m, 2H), 1.88-1.92 (m, 2H), 2.59-3.03 (m, 16H), 3.60 (s, 2H), 3.91 (s, 6H), 6.44 (s, 2H); $^{13}$C NMR ($D_2O$) δ 26.75, 27.91, 48.34, 49.21, 49.89, 50.96, 52.01, 52.86, 54.88, 57.15, 57.53, 59.42, 142.65, 157.42, 166.42; FAB MS m/z 352 (M+H); Anal. ($C_{18}H_{33}N_5O_2$ 4.1 HBr 0.25$H_2O$); Calc. C, 31.44; H, 5.51; N, 10.18; Br, 47.64. Found C, 31.17; H, 5.61; N, 9.92; Br, 47.54.

EXAMPLE 20

1-[2-Chloropyrid-4-yl(methylene)]-1,4,8,11-tetraazacyclotetradecane Tetrahydrochloride Monohydrate (AMD 7048)

$^{1}$H NMR ($D_2O$) δ 1.92 (m, 2H), 2.12 (m, 2H), 2.77-2.80 (m, 4H), 2.96-3.39 (m, 12H), 3.85 (s, 2H), 7.33 (d, 1H, J=5.4 Hz), 7.44 (s, 1H), 8.40 (d, 1H, J=5.4 Hz); $^{13}$C NMR ($D_2O$) δ 24.75, 27.59, 47.40, 47.55, 49.11, 49.23, 52.12, 52.40, 53.81, 54.42, 56.98, 126.97, 128.30, 151.90, 152.34, 153.78; FAB MS m/z 326 (M+H); Anal. ($C_{16}H_{28}N_5Cl$.4.2HCl.0.5HOAc.1.1$H_2O$); Calc. C, 38.61; H, 6.94; N, 13.24; Cl, 34.86. Found C, 38.63; H, 6.94; N, 13.52; Cl, 34.61.

EXAMPLE 21

1-[2,6-Dimethylpyrid-4-yl(methylene)]-1,4,8,11-tetraazacyclotetradecane Pentahydrobromide Dihydrate (AMD 7060)

$^{1}$H NMR ($D_2O$) δ 1.77 (m, 2H), 1.93 (m, 2H), 2.48 (s, 6H), 2.61-3.00 (m, 16H), 3.61 (s, 2H), 7.07 (s, 2H); $^{13}$C NMR ($D_2O$) δ 25.30, 26.22, 27.49, 47.75, 48.65, 49.43, 50.41, 51.58, 52.19, 54.09, 56.63, 58.46; FAB MS m/z 320 (M+H); Anal. ($C_{18}H_{33}N_5$.5HBr.0.5HOAc.1.7$H_2O$); Calc. C, 29.08; H, 5.57; N, 8.92; Br, 50.91. Found C, 29.04; H, 5.60; N, 8.73; Br, 50.87.

EXAMPLE 22

1-[2-Methylpyrid-4-yl(methylene)]-1,4,8,11-tetraazacyclotetradecane Pentahydrobromide Dihydrate (AMD 7061)

$^{1}$H NMR ($D_2O$) δ 2.01-2.08 (m, 2H), 2.22 (m, 2H), 2.70-2.72 (m, 2H), 2.77 (s, 3H), 2.91-2.92 (m, 2H), 3.33-3.52 (m, 12H), 4.00 (s, 2H), 7.86-7.89 (m, 2H), 8.56 (d, 1H, J=5.7 Hz); FAB MS m/z 306 (M+H); Anal. ($C_{17}H_{31}N_5$.4.9HBr.0.3HOAc.2.1$H_2O$); Calc. C, 27.9; H, 5.49; N, 9.24; Br, 51.67. Found C, 28.08; H, 5.50; N, 9.56; Br, 51.56.

EXAMPLE 23

1-[2,6-Dichloropyrid-4-yl(methylene)]-1,4,8,11-tetraazacyclotetradecane Trihydrochloride Bishydrate (AMD 3451)

$^{1}$H NMR ($D_2O$) δ 1.83-1.88 (m, 2H), 2.04-2.08 (m, 2H), 2.58-2.62 (m, 2H), 2.79-2.81 (m, 2H), 3.12-3.44 (m, 12H), 3.69 (s, 2H), 7.30 (s, 2H); $^{13}$C NMR ($D_2O$) □□36.26, 37.69, 55.26, 56.18, 58.33, 58.56, 58.92, 59.23, 63.57, 65.44, 70.72, 140.37, 166.14, 167.37; FAB MS m/z 360 (M+H). Anal. ($C_{16}H_{34}N_5Cl_5O_2$): Calc. C, 38.00;H, 6.78; N, 13.85; Cl, 35.05. Found: C, 38.33; H, 6.42; N, 13.88; Cl, 35.43.

EXAMPLE 24

1-[2-Chloropyrid-5-yl(methylene)]-1,4,8,11-tetraazacyclotetradecane Tetrahydrochloride Hemihydrate (AMD 3454)

$^{1}$H NMR ($D_2O$) δ 1.96-2.09 (br m, 4H), 3.02-3.17 (m, 4H), 3.19-3.28 (br m, 8H), 3.40 (s, 4H), 4.10 (s, 2H), 7.40 (d, 1H, J=8.2 Hz), 7.80 (d, 1H, J=8.2 Hz), 8.27 (s, 1H); $^{13}$C NMR ($D_2O$) δ 19.36, 19.47, 38.17, 38.64, 39.06, 41.74, 41.88, 42.18, 45.66, 48.29, 54.62, 125.59, 126.69, 142.79, 150.77, 151.75; FAB-MS m/z 326 (M+H). Anal. Calcd for $C_{16}H_{28}N_5Cl$.4HCl.0.5$H_2O$: C, 39.98; H, 6.92; N, 14.57; Cl, 36.87. Found: C, 40.36; H, 7.06; N, 14.56; Cl, 36.92.

General Procedures A, B and C were used to prepare the following compounds:

EXAMPLE 25

N-[1,4,8,11-Tetraazacyclotetradecanyl-1,4-phenylenebis(methylene)]-purine Pentahydrobromide DiHydrate (AMD3472)

$^{1}$H NMR ($D_2O$) δ 1.88-2.05 (br m, 4H), 3.06-3.22 (br m, 8H), 3.27-3.44 (br m, 8H), 4.22 (s, 2H), 5.59 (s, 2H), 7.29 (s, 4H), 8.80 (s, 1H), 9.11 (s, 1H), 9.28 (s, 1H); $^{13}$C NMR ($D_2O$) δ 18.39, 19.25, 37.24, 37.55, 37.71, 41.13, 41.37, 41.71, 44.41, 47.73, 54.87, 129.45, 131.81, 132.53, 136.67, 140.96, 147.88, 152.46, 154.37; FAB-MS m/z 423 (M+H). Anal. Calcd for $C_{23}H_{34}N_8$.5HBr.2$H_2O$.0.5$CH_3CO_2H$: C, 32.27; H, 5.07; N, 12.54; Br, 44.73. Found: C, 32.66; H, 4.81; N, 12.41; Br, 44.58.

EXAMPLE 26

1-[1,4,8,11-Tetraazacyclotetradecanyl-1,4-phenylenebis(methylene)]-4-phenylpiperazine Pentahydrobromide Hydrate (AMD3526)

$^{1}$H NMR ($D_2O$) δ 1.88-2.06 (br m, 4H), 3.11-3.53 (br m. 24H), 4.30 (s, 2H), 4.32 (s, 2H), 6.89-6.97 (m, 3H), 7.19-7.24 (m, 2H), 7.49 (s, 4H); $^{13}$C NMR ($D_2O$) δ 18.74, 19.37, 37.34, 41.47, 41.76, 42.03, 44.31, 47.45, 48.26, 51.16, 58.48, 59.29, 118.18, 122.34, 129.99, 130.37, 131.53, 131.85, 132.62, 148.47; FAB-MS m/z 547 (M+H$^{81}$Br), 545 (M+H$^{79}$Br), 465 (M+H). Anal. Calcd for $C_{28}H_{44}N_6 \cdot 5HBr \cdot H_2O$: C, 37.90; H, 5.79; N, 9.47; Br, 45.03. Found: C, 37.72; H, 5.98; N, 9.38; Br, 46.78.

TABLE 4

| Compound | IC$_{50}$[a] (µg/mL) |
|---|---|
| AMD3451 | 8.9 |
| AMD3472 | 45.4 |
| AMD3454 | 32.3 |
| AMD3526 | 82 |
| AMD3100 | >100 |

[a]50% Inhibitory Concentration (IC$_{50}$)(µg/mL) exhibited by AMD compounds against infection of U87.CD4.CCR5 by HIV-1 BaL

EXAMPLE 27

Inhibition of Collagen-Induced Arthritis

A compound as used in the present invention demonstrated inhibition of collagen-induced arthritis (CIA) in a mutant mouse model.

Methodology

Experimental Animal Treatment

Figure 27:
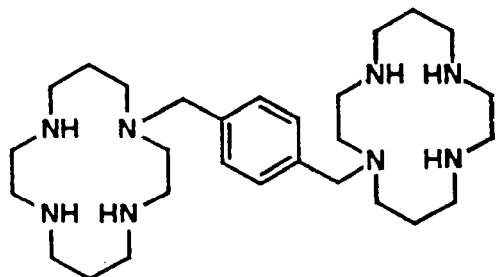
FIG. 27; shows the structural formula of compound AMD 3100.

The control group consisted of ten mice that were injected with collagen as discussed below. The treatment group consisted of eight mice which were also injected with collagen and were further treated by administering a compound of (1,1'-[1,4-phenylenebis(methylene))]bis-1,4,8,11-tetraazacyclotetradecane) (AMD 3100; see FIG. 27) intravenously using osmotic pumps (20011, Alza, 0.5 µl/hr) at a concentration of 5 mg/ml over a 14-day period following collagen injection.

Mutant Mice

The generation and the basic characteristics of the mutant mouse strain (129/Sv/Ev) with a disruption in the gene coding for the α-chain of the IFN-γ receptor (IFN-γ RKO) have been described (Huang S. et al., Science 259:1742, (1993)). These IFN-γ RKO mice were back-crossed with DBA/1 wild-type mice for 10 generations to obtain the DBA/1 IFN-γ RKO mice used in the present study. IFN-γ RKO and wild-type mice were bred in the Experimental Animal Centre of the University of Leuven. The experiments were performed in 8- to 12-week old mice, but in each experiment, the mutant and wild-type mice were age-matched with a 5 day limit. The male to female ratio was kept between 0.8 and 1.3 in each experimental group.

Induction of Collagen-Induced Arthritis and Clinical Assessment of Arthritis

Collagen-induced arthritis was carried out in the following manner (see: Vermeire et al., Int. J. Immunol. 158:5507-5513, (1997)). Native chicken collagen type II (EPC, Owensville, Mo.) was dissolved in 0.05 M acetic acid at 2 mg/ml by stirring overnight at 6° C., and emulsified in an equal volume of incomplete (IFA) or complete Freund's adjuvant (CFA) containing 1.5 mg/ml heat killed Mycobacterium butyricum (Difco, Detroit, Mich.). Mice were sensitized with a single 100 µl intradermal injection of the emulsion at the base of the tail. Mice were examined daily for signs of arthritis. The disease severity was recorded following a scoring system for each limb. Score 0: normal; score 1: redness and/or swelling in one joint; score 2: redness and/or swelling in more than one joint; score 3: redness and/or swelling in the entire paw; score 4: deformity and/or ankylosis.

Histological Examination

Spleens and fore and hind limbs were fixed in buffered saline—B5fixative (10% formalin with quicksilver). Alternatively, tissues were fixed in 10% formalin or pure methanol (see: Vermeire et al., J. Immunol., 158, 5507-5513, 1997). Limbs were subsequently decalcified overnight with formic acid. Four-micron thick paraffin sections were stained with hematoxylin and eosin. Severity of arthritis was evaluated using three parameters: infiltration of mono-and polymorphonuclear cells, hyperplasia of the synovium and parmus formation. Each parameter was scored on a scale from 0 to 3 (absent; weak, moderate and severe).

In Vivo Antibody Treatments

Monoclonal antibodies were produced from hybridomas grown by intraperitoneal inoculation in Pristane-primed athymic nude mice (nu/nu of NMRI background). Neutralizing monoclonal antibody against MuIFN-γ (F3, rate IgG$_{24}$) was purified by affinity chromatography on a mouse anti-rat κ chain monoclonal antibody (Billiau A. et al., J. Immunol. 140:1506, (1988)). The neutralizing titer (end-point dilution corresponding to 50% neutralization of the antiviral effect of 30 units/ml of mouse IFN-γ on mouse 1929 cells challenged with mengovirus) was 10$^{5.3}$ U/ml (IgG content, 1.4 mg/ml). A neutralizing rate IgG$_{24}$ antibody against murine IL-12 was produced using hybridoma C17.8 (kindly provided by Dr. G. Trinchieri, Wistar Institute, Philadelphia, Pa.). The antibody was purified by affinity chromatography on protein G (Pharmacia, Uppsala, Sweden). Antibody against murine IL-6 was prepared from ascites fluid from thymus-less nude mice inoculated with the 20F3 (rat x mouse) hybridoma (American Type Culture Collection, Rockville, Md.). This rat IgG antibody was purified by affinity chromatography on an anti-rat K chain monoclonal antibody-Sepharose column. The neutralizing titer (endpoint dilution corresponding to 50% neutralization of the cell growth effect of 10 U of murine IL-6 per ml) was 10$^{5.5}$ (IgG content: 2.9 mg/ml). Irrelevant rat IgG$_{24}$ was used as an isotype control and was prepared from ascites fluid of a rat plasmocytoma (obtained through the courtesy of Dr. H. Bazin, University of Louvain, Medical School, Brussels, Belgium). The IgG was purified by anion exchange chromatography on Hiload Q Sepharose and gel filtration on Superdex 200 (Pharmacia). Batches of anti-IFN-γ, anti-IL-12, anti-IL-6 and irrelevant IgG$_{24}$ were tested for endotoxin content by a chromogenic Limulus amoebocyte lysate assay (KabiVitrurm, Stockholm, Sweden) and were found to contain less than 2 ng/ml endotoxin. Injections were given in 200 µl of pyrogen-free saline.

Results

Figure 29:
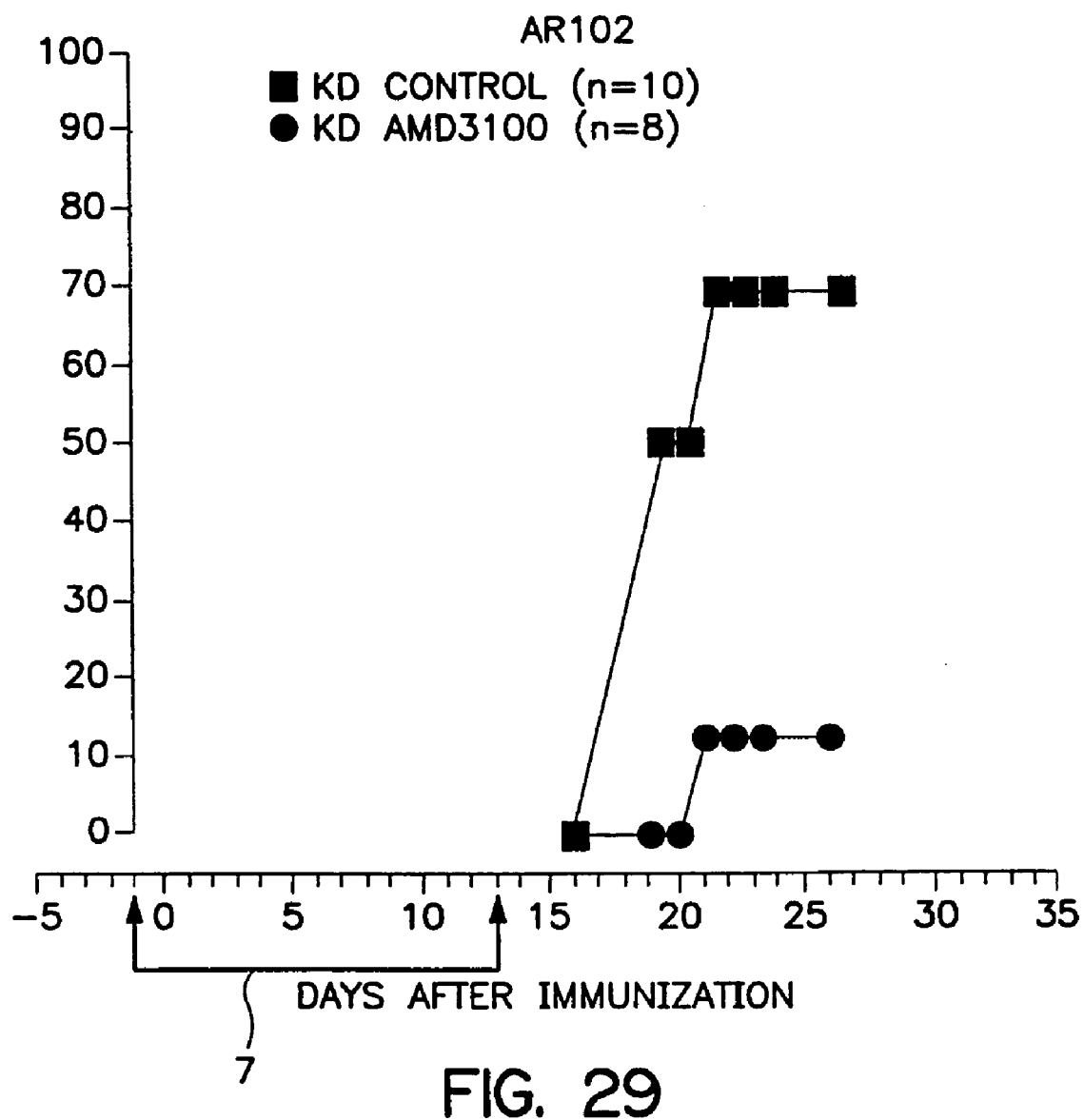
FIG. 29, shows the cumulative incidence of collagen-induced arthritis in laboratory animals following treatment or immunization with compound AMD 3100.
Figure 30:
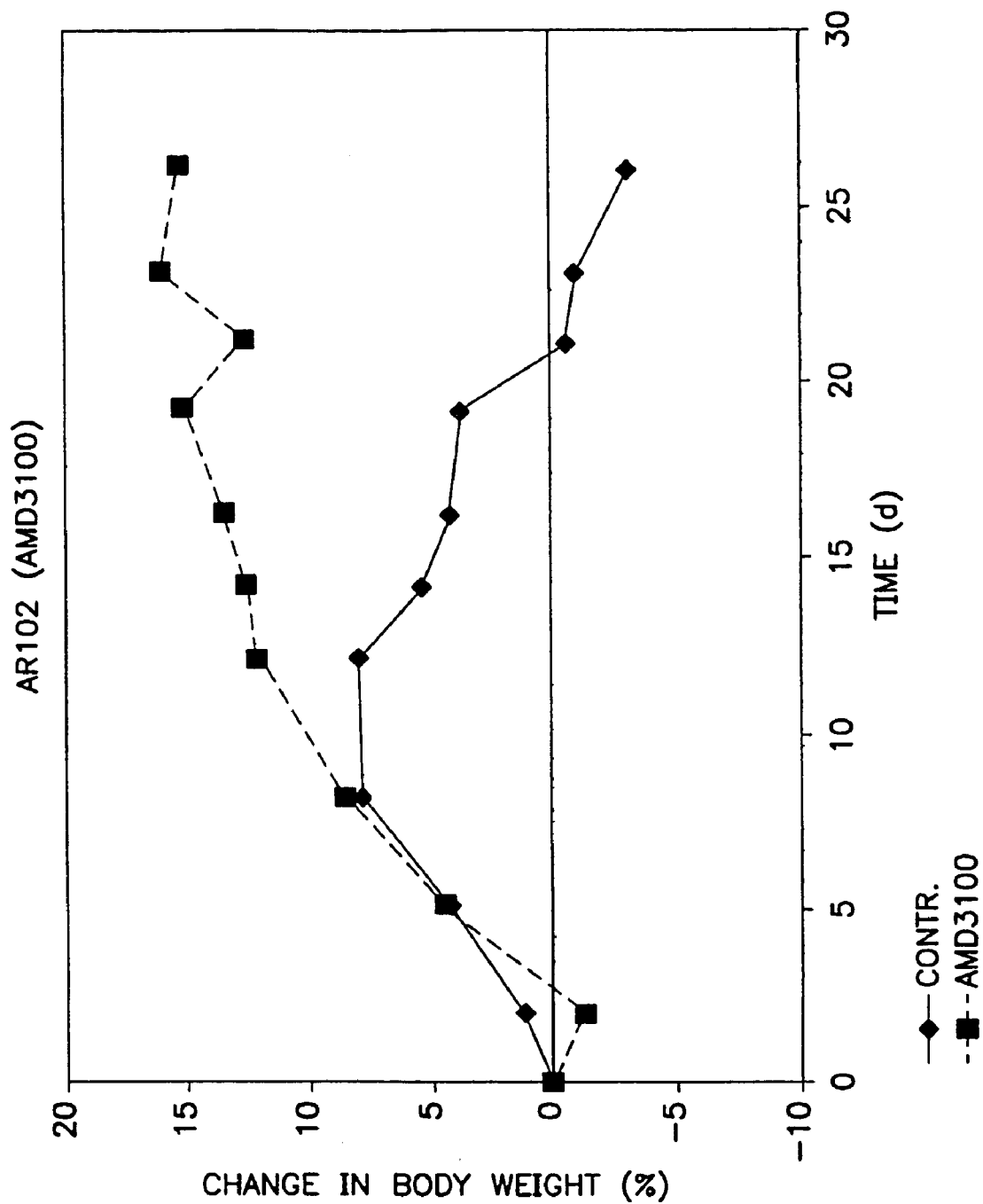
FIG. 30, shows the change in body weight of laboratory animals following treatment with compound AMD 3100.
Figure 31:
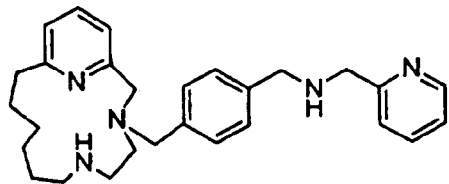
FIG. 31, shows the structural formula of compound AMD 8630.
Figure 32:
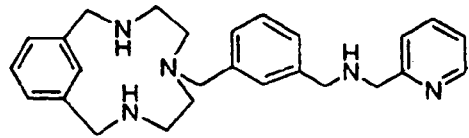
FIG. 32, shows the structural formula of compound AMD 7097.
Figure 33:
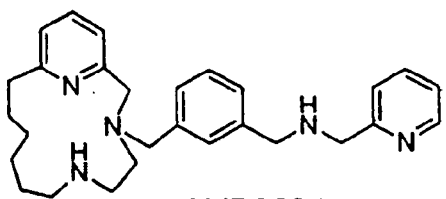
FIG. 33, shows the structural formula of compound AMD 8631.

Following 14 days after treatment, 7 of the ten mice in the control group demonstrated arthritis, while only 1 of the 8 treated animals demonstrated disease. See FIG. 29. The single treated animal did not develop arthritic pathology until after 20 days post-treatment. Additionally, the treated animals compared with the control animals did not demonstrate any significant body weight loss. See FIG. 30. Further, the treated animals maintained body weight consist with healthy animals not injected with collagen (curve not shown).

EXAMPLE 28

Treatment of Glioblastoma

Compounds of the present invention, such as AMD 3100 may be used in the treatment of glioblastomas, fibromas, astrocytomas or myelomas affecting the central nervous system. The compounds may be used according to standard clinical practice and procedures, using dosages as provided in the foregoing examples and according to clinical end points, such as imaging, immunological and other methodologies.

For example, the etiology or association of chemokine receptor binding in the proliferation of glioblastoma tumor cells has been reported by Sehgal et al., *J. of Surg. Oncolo.* 69:99-104 (1998) ("Sehgal I") and Sehgal et al., *J. of Surg. Oncolo.* 69:239-248 (1998) ("Sehgal II"). The role of CXCR4 of its binding to its receptor appears to play a significant role in the formation and/or proliferation of glioblastoma cells. The inhibition of the binding by CXCR4 to its natural receptor ligand by compounds of the present invention, such as AMD 3100, offer a new drug in the treatment tumors of central nervous system that are mediated or associated with chemokines, such as CXCR4.

EXAMPLE 29

Treatment of Non-Small Cell Lung Cancer

Compounds of the present invention, such as AMD 3100, may be used in the treatment of non-small cell lung cancer. The compounds may be used according to standard clinical practice and procedures, using dosages as provided in the foregoing examples and according to clinical end points, such as imaging, immunological and other methodologies.

For example, CXC chemokines have been found to regulate or are associated with the regulation of angiogenesis in non-small cell lung cancer (see: Arenberg, et al., *J. of Leukocyte Biol.*; 62:554562 (1997); and Moore et al. *TCM*, vol 8(2): 51-58 (1998) Elsevier Science, Inc.). The role of CXC chemokines and the binding to their respective receptors appear to play a significant role in the formation and/or proliferation of non-small cell lung cancer promoted by an increase in angiogenic activity. The inhibition of the binding of these CXC chemokines to their natural receptor ligands by compounds of the present invention, such as AMD 3100, offer a new drug in the treatment tumors such as non-small cell lung cancer that are mediated or associated with increased levels of chemokines.

EXAMPLE 30

Figure 34:
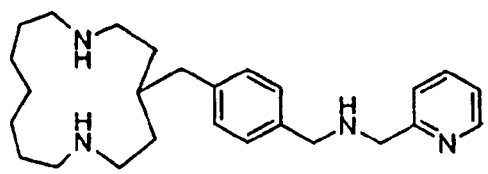
FIG. 34, shows the structural formula of compound AMD-Exp 1.
Figure 35:
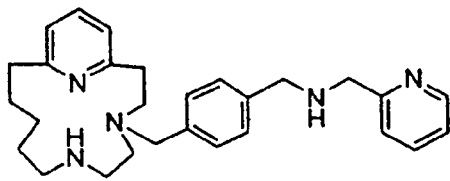
FIG. 35, shows the structural formula of compound AMD 7450.

N-[4-(1,7-Diazacyclotetradecanyl)-1,4-phenylenebis(methylene)]-2-(aminomethyl)pyridine The compounds of the present invention further include compounds of formula I, where V has 2 to 6 optionally substituted amine nitrogens spaced by two or more optionally substituted carbon atoms from each other. An example of such compound, includes:

N-[4-(1,7-Diazacyclotetradecanyl)-1,4-phenylenebis(methylene)]-2-(aminomethyl)pyridine (AMD-Exp 1; see FIG. 34).

AMD-Exp 1, Exp-2 and Exp3 may each be prepared by modification of our previously published strategies (Bridger et al. *J. Med. Chem.* 1995, 38, 366) for preparing carbon-linked azamacrocycles and is briefly summarized as follows: The aformentioned intermediate, N-[1-methylene-4-(chloromethylene)phenylene]-N-(2-nitrobenzenesulfonyl)-2-aminomethyl)pyridine (or the Dep-protected intermediate) is reacted with the sodium salt of diethylmalonate to give the corresponding diester.

Reduction of the diester to the corresponding diol, followed by derivatization with methanesulfonyl chloride gave the dimesylate. Nucleophilic displacement of the dimesylate with sodium cyanide gives the requisite dinitrile which was reduced to the diamine with borane.THF and derivatized with 2-nitrobenzenesulfonyl chloride for the impending macrocyclization reaction.

Macrocyclization with an appropriately derivatized diol (such as 1,7-heptanediol di-p-tosylate) and subsequent deprotection as described in previous examples gave, for example, AMD-Exp 1. Similarly, 1,3-phenylenediethanol and 2,6-pyridine diethanol would give AMD-Exp 2 and AMD-Exp-3 respectively.

Further, AMD-Exp 1, AMD-Exp 2, and AMD-Exp 3 may each be prepared into a pharmaceutical compositions comprising a therapeutically effective amount of the compound in a pharmaceutically acceptable carrier.

Additionally, AMD-Exp 1, AMD-Exp 2, and AMD-Exp 3 may each be used according to the foregoing methods for the treatment of a number of chemokine-mediated diseases and conditions, including: infection with HIV or FIV; a disease by the regulation of endothelial cell function; a disease relating to vascularization of the gastrointestinal tract; haematopoiesis; or cerebellar development; a disease relating to basal leukocyte trafficking or the extravasation and tissue infiltration of leukocytes in response to inciting antigens; compound effectively binds to a chemokine receptor; of inflammatory disease; cancer; central nervous system developmental disease; HIV; FIV; vasculature development disease; cardiogenesis developmental disease; haematopoiesis and other chemokine mediated diseases or disorders.

Additional examples of such specific diseases or conditions that may be treated using AMD-Exp 1, further include: inflammation due to arthritis or multiple sclerosis; cancers associated with: solid tumors; lymphoma; metastatic tumors; glioblastoma tumors; and other carcinoma tumors; non-small cell lung cancer; lung cancer; breast cancer; prostate cancer; and cancer of other organs. Further, disorders or conditions that may be treated using AMD-Exp 1, includes: disorders treated by inhibiting or promoting angiogenesis or by inducing stasis of angiogenesis.

EXAMPLE 31

Figure 36:
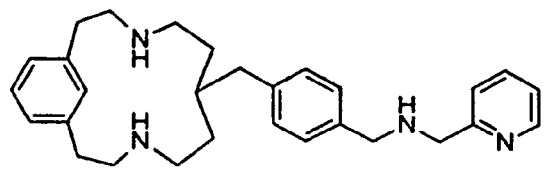
FIG. 36, shows the structural formula of compound AMD-Exp 2.
Figure 37:
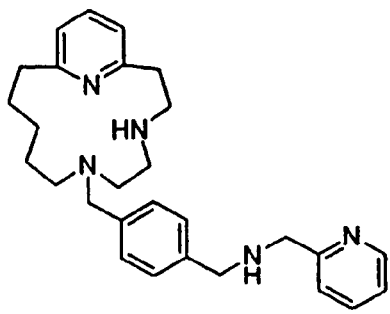
FIG. 37, shows the structural formula of compound AMD 7463.
Figure 38:
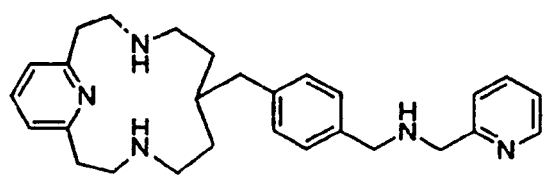
FIG. 38, shows the structural formula of compound AMD-Exp 3.

N-[7-(4,10-Diazabicyclo[13.3.1]heptadeca-1(17),13,15-trienyl)-1,4-phenylenebis(methylene)]-2-(aminomethyl)pyridine The compounds of the present invention further include compounds of formula I, where V has 2 to 6 optionally substituted amine nitrogens spaced by two or more optionally substituted carbon atoms from each other. An example of such compound, includes:

N-[7-(4,10-Diazabicyclo[13.3.1]heptadeca-1(17), 13,15-trienyl)-1,4-phenylenebis(methylene)]-2-(aminomethyl)pyridine (AMD-Exp 2; see FIG. 36).

AMD-Exp 2 and AMD-Exp 3 may each be prepared according to Exampel 30 above. Further, AMD-Exp 2 may be prepared into a pharmaceutical compositions comprising a therapeutically effective amount of the compound in a pharmaceutically acceptable carrier.

Additionally, AMD-Exp 2 may be used according to the foregoing methods for the treatment of a number of chemokine-mediated diseases and conditions, including: infection with HIV or FIV; a disease by the regulation of endothelial cell function; a disease relating to vascularization of the gastrointestinal tract; haematopoiesis; or cerebellar development; a disease relating to basal leukocyte trafficking or the extravasation and tissue infiltration of leukocytes in response to inciting antigens; compound effectively binds to a chemokine receptor; of inflammatory disease; cancer; central nervous system developmental disease; HIV; FIV; vasculature development disease; cardiogensis developmental disease; haematopoiesis and other chemokine mediated diseases or disorders.

Additional examples of such specific diseases or conditions that may be treated using AMD-Exp 2, further include: inflammation due to arthritis or multiple sclerosis;

cancers associated with: solid tumors; lymphoma; metastatic tumors; glioblastoma tumors; and other carcinoma tumors; non-small cell lung cancer; lung cancer; breast cancer; prostate cancer; and cancer of other organs. Further, disorders or conditions that may be treated using AMD-Exp 2, includes: disorders treated by inhibiting or promoting angiogenesis or by inducing stasis of angiogenesis.

The active compounds may be administered in the form of a pharmaceutical composition formulated according to well known principles and incorporating the compound, preferably in unit dose form, in combination with a pharmaceutically acceptable diluent, carrier or excipient. Such compositions may be in the form of solutions or suspensions for injection, or irrigation or be in capsule, tablet, dragee, or other solid composition or as a solution or suspension for oral administration or formulated into pessaries or suppositories or sustained release forms of any of the above for implantation. Suitable diluents, carriers, excipients and other components are well known. It may be desirable also to formulate a composition for topical administration such as an ointment or cream. The compounds of the invention may be used, in the form of a composition or alone.

The pharmaceutical compositions according to the invention may be formulated in unit dosages determined in accordance with conventional pharmacological methods, suitably to provide active compounds in the dosage range in humans or animals of from 0.01 to 100 mg/kg body weight per day, in a single dose or in a number of smaller doses. Preferred dosage ranges are 0.01 to 30 mg/kg body weight per day intravenous (iv) or intraperitoneal (ip). Other active compounds may be used in the compositions or such active compounds or supplemental therapy may be included in a course of treatment. The pharmaceutical compositions are useful for treatment of a patient comprising an effective therapeutic amount of the novel compound, where said compound effectively binds to a chemokine receptor.

The present invention further contemplates the use of these compositions in the manufacture of a medicament for the treatment of HIV-or FIV-infected patients and/or the treatment of a disease by the regulation of endothelial cell function and/or the treatment of a disease relating to vascularization of the gastrointestinal tract; haematopoiesis; or cerebellar development.

In a method for treating a patient infected with HIV or FIV, the pharmaceutical composition is administered to said patient as a therapeutically effective amount of a pharmaceutical composition in a pharmaceutically acceptable carrier. In a method of treating a patient with a disease related to the regulation of endothelial cell function, the pharmaceutical composition is administered to said patient as a therapeutically effective amount of a pharmaceutical composition in a pharmaceutically acceptable carrier. The present invention further contemplates methods of treating a patient with a disease relating to vascularization of the gastrointestinal tract; haematopoiesis; or cerebellar development, by administering to said patient a therapeutically effective amount of a pharmaceutical composition in a pharmaceutically acceptable carrier.

The present invention further contemplates a method of treating a patient with a disease relating to basal leukocyte trafficking or the extravasation and tissue infiltration of leukocytes in response to inciting antigens, by administering to said patient a therapeutically effective amount of a pharmaceutical composition in a pharmaceutically acceptable carrier. The present method also contemplates treating a patient, by administering to said patient a therapeutically effective amount of a pharmaceutical composition in a pharmaceutically acceptable carrier, wherein said compound effectively binds to a chemokine receptor.

The present invention further contemplates pharmaceutical compositions and methods of use for the treatment of humans or animals for: renal allograft rejection; inflammatory disease; cancer; central nervous system developmental disease; HIV; vasculature development disease; haematopoiesis and other chemokine mediated diseases or disorders. This invention further provides for the treatment of diseases, which include, but are not limited to: arthritis; multiple sclerosis; dementia from HIV or FIV infection, Parkinson's disease, Alzheimer's disease and inflammatory diseases. The pharmaceutical compositions and methods of use of the present invention further provide for the treatment of cancers, that include, but are not limited to those associated with: solid tumors; lymphoma; metastatic tumors; glioblastoma tumors; and other carcinomas tumors. The pharmaceutical compositions of the present invention are useful for the treatment of cancers that include, but are not limited to: non-small cell lung cancer; lung cancer; breast cancer; prostate cancer; and cancer of other organs.

Other diseases or disorders that are contemplated to be treated with the pharmaceutical compositions of the present invention, include, but are not limited to: disorders treated by inhibiting or promoting angiogenesis or by inducing stasis of angiogenesis; developmental disorders mediated by chemokines.

The present invention further provides methods for the prevention of a disease or disorder in a patient by administering a therapeutically effective dosage of the pharmaceutical compositions of the present invention to a patient over a period of time sufficient to effectively prevent the disease or disorder.

The invention claimed is:

1. A method for treating or ameliorating at least one disorder mediated by CXCR4 comprising administering to a subject in need of such treatment an effective amount of N-[1,4,8,11-tetraazacyclotetradecanyl-1,4-phenylenebis(methylene)]-2-(aminomethyl)pyridine or a pharmaceutically acceptable salt thereof or a pharmaceutical composition thereof, wherein said disorder is arthritis, glioblastoma, non-small cell lung cancer, lymphoma, vasculature development disease of the gastrointestinal tract, a disorder comprising basal leukocyte trafficking, or a disorder comprising extravasation and tissue infiltration of leukocytes in response to inciting antigens.

2. The method of claim 1, wherein said disorder is arthritis.

3. The method of claim 1, wherein said disorder is glioblastoma.

4. The method of claim 1, wherein said disorder is non-small cell lung cancer.

5. The method of claim 1 wherein the disorder is lymphoma.

6. The method of claim 1 wherein the disorder is vasculature development disease of the gastrointestinal tract.

7. The method of claim 1 wherein the disorder comprises basal leukocyte trafficking.

8. The method of claim 1 wherein the disorder comprises extravasation and tissue infiltration of leukocytes in response to inciting antigens.

* * * * *